(12) United States Patent
Pandey et al.

(10) Patent No.: US 11,065,235 B2
(45) Date of Patent: Jul. 20, 2021

(54) SUBSTITUTED METHANOPYRIDO [2, 1-A] ISOINDOLONES AS MACHR MODULATORS FOR TREATING VARIOUS ASSOCIATED PATHOPHYSIOLOGICAL CONDITIONS AND PROCESS FOR PREPARATION THEREOF

(71) Applicants: COUNCIL OF SCIENTIFIC & INDUSTRIAL RESEARCH, New Delhi (IN); CENTRE FOR BIOMEDICAL RESEARCH, Lucknow (IN)

(72) Inventors: Ganesh Pandey, Lucknow (IN); Rajesh Varkhedkar, Lucknow (IN); Divya Tiwari, Lucknow (IN); Prem Narayan Yadav, Lucknow (IN); Shalini Dogra, Lucknow (IN); Yusuf Hussain, Lucknow (IN)

(73) Assignees: Council of Scientific & Industrial Research, New Delhi (IN); Centre for Biomedical Research, Uttar Pradesh (IN)

( * ) Notice: Subject to any disclaimer, the term of this patent is extended or adjusted under 35 U.S.C. 154(b) by 0 days.

(21) Appl. No.: 16/614,482

(22) PCT Filed: May 18, 2018

(86) PCT No.: PCT/IN2018/050317
§ 371 (c)(1),
(2) Date: Nov. 18, 2019

(87) PCT Pub. No.: WO2018/211530
PCT Pub. Date: Nov. 22, 2018

(65) Prior Publication Data
US 2020/0121657 A1    Apr. 23, 2020

(30) Foreign Application Priority Data
May 19, 2017 (IN) .............................. 201711017657

(51) Int. Cl.
| | | |
|---|---|---|
| *A61K 31/439* | (2006.01) |
| *A61P 25/28* | (2006.01) |
| *A61K 31/437* | (2006.01) |
| *A61K 45/06* | (2006.01) |
| *C07D 471/04* | (2006.01) |
| *C07D 471/08* | (2006.01) |

(52) U.S. Cl.
CPC .......... *A61K 31/439* (2013.01); *A61K 31/437* (2013.01); *A61K 45/06* (2013.01); *A61P 25/28* (2018.01); *C07D 471/04* (2013.01); *C07D 471/08* (2013.01)

(58) Field of Classification Search
CPC .. C07D 471/04; C07D 471/08; A61K 31/439; A61K 45/06; A61P 25/28
See application file for complete search history.

(56) References Cited

U.S. PATENT DOCUMENTS

| | | | |
|---|---|---|---|
| 7,067,507 B2 * | 6/2006 | Pulley | .................... A61P 43/00 514/183 |
| 2009/0111830 A1 | 4/2009 | Wagenen et al. | |
| 2013/0196978 A1 | 8/2013 | Caligiuri et al. | |
| 2013/0225624 A1 | 8/2013 | Fisher et al. | |
| 2013/0267706 A1 | 10/2013 | Ji et al. | |
| 2013/0331364 A1 | 12/2013 | Hughes et al. | |
| 2014/0051864 A1 | 2/2014 | Ji et al. | |
| 2014/0148420 A1 | 5/2014 | Gras Escardo et al. | |

FOREIGN PATENT DOCUMENTS

| | | |
|---|---|---|
| CN | 103242214 A | 8/2013 |
| CN | 103502213 A | 1/2014 |
| WO | 0107406 A1 | 2/2001 |
| WO | 2010047990 A1 | 4/2010 |
| WO | 2013103931 A1 | 7/2013 |
| WO | 2013106795 A1 | 7/2013 |
| WO | 2013122107 A1 | 8/2013 |
| WO | 2013126856 A1 | 8/2013 |

(Continued)

OTHER PUBLICATIONS

Varkhedkar. ChemMedChem, 2018, 13, 384-395 (Year: 2018).*
Orii. BioScience Trends, 2010, 4(5), 260-266 (Year: 2010).*
International Search Report and Written Opinion dated Jul. 10, 2018 in PCT/IN2018/050317 filed May 18, 2018.
Gosens et al., "Muscarinic Reeptor Signaling in the Pathophysiology of Asthma and COPD," Respiratory Research. vol. 7, Article 73, pp. 1-15 (2006).
Petrie, et al., "Comparison of Aerosol Ipratropium Bromide and Salbutamol in Chronic Bronchitis and Asthma," British medical Journal, vol. 1, No. 5955, pp. 430-432, (1975).
Peter J. Barnes, et al., "Tiotropium Bormide," Expert Opinion on Investigational Drugs, vol. 10, No. 4, pp. 733, 2001.

(Continued)

*Primary Examiner* — Noble E Jarrell
(74) *Attorney, Agent, or Firm* — Dinsmore & Shohl LLP

(57) ABSTRACT

The present invention relates to substituted methanopyrido [2,1-a]isoindolones of formula I, wherein, $R^1$ is selected from phenylsulfonyl or p-toluenesulfonyl; and n=1, 2, 3; their derivatives, stereoisomers, pharmaceutically acceptable salts and pharmaceutically acceptable compositions having potential muscarinic acetylcholine receptor modulator activity.

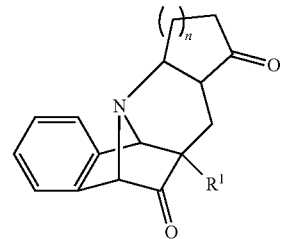

Formula I

16 Claims, 5 Drawing Sheets

(56) References Cited

FOREIGN PATENT DOCUMENTS

| WO | 2014014698 A2 | 1/2014 |
|---|---|---|
| WO | 2014035829 A1 | 3/2014 |
| WO | 2014045031 A1 | 3/2014 |

OTHER PUBLICATIONS

Ryo Orii, et al., "M3 Muscarinic Receptors Mediate Acetylcholine-induced Pulmonary Vasodilation in Pulmonary Hypertension," BioScience Trends, 4(5), pp. 260-266, (2010).

H. Du, et al., "Pancuronium Increases Pulmonary Arterial Pressure in Lung Injury," British Journal of Anesthesia, vol. 77, pp. 526-529, (1996).

Robert D. Harvey, et al., "Muscarinic Regulation of Cardiac Ion Channels," British Journal of Pharmacology, 139, pp. 1074-1084, (2003).

Jean-Louis Bény, et al. "Muscarinic Receptor Knockout Mice Confirm Involvement of M3 Receptor in Endothelium-Dependent Vasodilation in Mouse Arteries," Journal of CardiovascPharmacol, vol. 51, No. 5, pp. 505-512, May 2008.

M.G.C. Hendriks, et al., "Characterization of the muscarinic Receptor Subtype Mediating Vasodilation in the Rat Perfused Mesenteric Vascular Bed Preparation," Journal Auton. Pharmacol., vol. 12, pp. 411-420, (1992).

Mark H, Schweitzer P. (Edited by L.A. Gould, MD), Drug Treatment of Cardiac Arrhythmias, Arch Intern Med, vol. 144, pp. 457, (1984).

E.A. Van der Zee, et al., "Localization of Pre- and postsynaptic cholinergic markers in rodent forebrain: A brief history and comparison of rat and mouse," Behavioural Brain Research, vol. 221, pp. 356-366, (2011).

Carruthers, et al., "The muscarinic system, cognition and schizophrenia," Neuroscience and Biobehavioral Reviews, 55, 393, (2015).

Green, et al., "Muscarinic and nicotinic receptor modulation of object and spatial n-back working memory in humans," Pharmacology, Biochemistry and Behavior, vol. 81, pp. 575-584, (2005).

Veroff, et al., "Efficacy of Xanomeline in Alzheimer Disease: Cognitive Improvement Measured Using the Computerized neuropsychological Test Batter (CNTB)," Alzheimer Disease and Associated Disorders, vol. 12, No. 4, pp. 340-312, (1998).

Shekhar, et al., "Selective Muscarinic Receptor Agonist Xanomeline as a Novel Treatment Approach for Schizophrenia," American Journal Psychiatry, 165 (8), pp. 1033-1039, Aug. 2008.

Carey, et al., "SCH 57790, a selective muscarinic M2 receptor antagonist, releases acetylcholine and produces cognitive enhancement in laboratory animals," European Journal of Pharmacology, 431 (2), pp. 189-200, (2001).

Brian Dean, "Cholinergic muscarinic receptors: new opportunities to treat psychiatric disorders," Future Med. Chem., 5 (13), pp. 1547-1549, (2013).

Schwarz, et al., "Selective Muscarinic Agonists for Alzheimer Disease Treatment," Alzheimer Disease: Therapeutic Strategies, 1994.

Kruse, et al., "Muscarinic acetylcholine receptors: novel opportunities for drug development," Nature Reviews Drug Discovery, 13, pp. 549-560, (2014).

Sedman, et al., "Preclinical and Phase 1 Clinical Characterization of CI-979/RU35926, A Novel Muscarinic Agonist for the Treatment of Alzheimer's Disease," Life Sciences, vol. 56, Nos. 11/12, pp. 877-882, (1995).

Pandey, et al., "An Efficient Access to Enantiopure 1,3-disubstituted Isoindolines from Selective Catalytic Fragmentation of Original Desymmetrized Rigid Overbred Template," The Royal Society of Chemistry, pp. 1-3, (2015).

Engelbert Ciganek, "The Catalyzed a-Flydroxyalkylation and z-Aminoalkylation of Activated Olefins (The Morita-Baylis-Hillman Reaction)," Organic Reactions, vol. 51, pp. 201-350, (1997).

Gupta, et al., "Metabolic Syndrome: What are the risks for humans?", BioScience Trends, 4(5), pp. 204-212, (2010).

Kelly, et al., "Locomotor Activity in D2 Dopamine Receptor-Deficient Mice Is Determined by Gene Dosage, Genetic Background, and Developmental Adaptations," The Journal of Neuroscience, 18(9), pp. 3470-3479, (May 1, 1998).

A. Ennaceur & J. Delacour, "A new one-trial test for neurobiological studies of memory in rats. 1: Behavioral data," Behavioural Brain Research, 31, pp. 47-59, (1988).

Webster, et al., "Using mice to model Alzheimer's dementia: an overview of the clinical disease and the preclinical behavioral changes in 10 mouse models", Frontiers in Genetics, vol. 5, Article 88, pp. 1-23, Apr. 2014.

\* cited by examiner

SUBSTITUTED METHANOPYRIDO [2, 1-A] ISOINDOLONES AS MACHR MODULATORS FOR TREATING VARIOUS ASSOCIATED PATHOPHYSIOLOGICAL CONDITIONS AND PROCESS FOR PREPARATION THEREOF

FIELD OF INVENTION

The present invention relates to substituted methanopyrido [2,1-a]isoindolones of formula I,

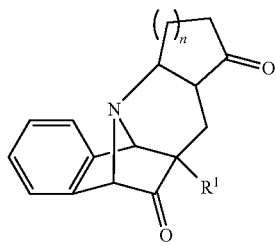

Formula I wherein, $R^1$ is selected from phenylsulfonyl or p-toluenesulfonyl; and n=1, 2, 3; their derivatives, stereoisomers, pharmaceutically acceptable salts and pharmaceutically acceptable compositions having potential muscarinic acetylcholine receptor modulator activity.

The present inventions also relates to a process for the preparation of compounds of formula I, their derivatives, their stereoisomers, their pharmaceutically acceptable salts and pharmaceutically acceptable compositions containing them.

The present invention also relates to the use of compounds of formula I in the treatment of various pathophysiological conditions that are related to muscarinic acetylcholine receptor functions, specifically COPD (chronic obstructive pulmonary disease), pulmonary hypertension, cardiovascular diseases, various disorders associated with CNS and brain such as cognition, learning & memory, mood disorder and ADHD (attention deficit hyperactivity disorders).

BACKGROUND OF THE INVENTION

G-protein coupled receptors (GPCRs) being most important membrane receptors for cellular communication in eukaryotes, regulates diverse array of function in human body. More than $⅓^{rd}$ of the present drug molecules act by binding with GPCRs. The muscarinic receptors are one of the important members of GPCRs family which are widely expressed in the human body.

Five different muscarinic acetylcholine receptors (mAChR) namely M1, M2, M3, M4 and M5 encoded by CHARM1 to CHARM5 genes have been identified and characterized by molecular cloning studies, which belong to the G-protein-coupled receptors. M1, M3 and M5 coupled to $G_{q/11}$ and stimulate the inositol phosphate pathway, whereas M2 and M4 coupled to $G_{i/o}$ and mediate inhibition of adenylyl cyclase activity.

The muscarinic M3 receptor activity of acetylcholine is associated with the pathophysiology of asthma and chronic obstructive pulmonary disease (COPD). The Vagal tone, which appears to be reversible, is increased in airway inflammation associated with asthma and COPD from exaggerated acetylcholine release and enhanced expression of downstream signalling components in airway smooth muscles. The muscarinic receptor signalling regulates airway smooth muscle thickening and differentiation [(R. Gosens, et al, "Muscarinic receptor signalling in the pathophysiology of asthma and COPD," *Respiratory Research*, vol. 7, article 73, 2006)].

Thus, muscarinic M3 receptor antagonists have been demonstrated to be effective in the treatment of the asthma and COPD. The ipratropium bromide which inhibits M1, M2 and M3 muscarinic receptors was the first compound for effective treatment of the patients with obstructive pulmonary diseases [(G. R. Petrie and K. N. V. Palmer, "Comparison of aerosol ipratropium bromide and salbutamol in chronic bronchitis and asthma," *British Medical Journal*, vol. 1, no. 5955, pp. 430, 1975)]. Moreover, tiotropium bromide which also binds the M1, M2 and M3 muscarinic receptors with slower dissociation rates are also used for treatment of patients with moderate to severe COPD [(P. J. Barnes, "Tiotropium bromide," *Expert Opinion on Investigational Drugs*, vol. 10, no. 4, pp. 733, 2001)].

Several congenital heart diseases (CHDs) are associated with pulmonary artery hypertension (PAH). It was recently established that muscarinic receptors mediates pulmonary circulatory vasodilator responses [(Ryo Orii, Yasuhiko Sugawara, Shigehito Sawamural, Yoshitsugu Yamada, *BioScience Trends*. 2010; 4(5):260)]. The pancuronium bromide, which is potent M2 and M3 muscarinic receptor antagonist, is known to increase pulmonary arterial pressure suggesting cholinergic vasodilation is involved in these muscarinic receptor and plays important role in regulating pulmonary hypertension [(Du H, Orii R, Yamada Y, Hayashida M, Kin N, Suwa K, Hanaoka K. Pancuronium increases pulmonary arterial pressure in lung injury. Br *J Anaesth*. 1996; 77:526)].

The muscarinic receptors are expressed through the cardiovascular system and play an important role in parasympathetic regulation of cardiovascular function. Activation of M2 muscarinic receptor affects conduction of electrical impulses through atrioventricular node, and also regulates electrical and mechanical activity of the atria and ventricles [(Harvey R D, Belevych A E (2003) Muscarinic regulation of cardiac ion channels. *Br J Pharmacol.*, 139, 1074)]. Importantly, activation of M3 and M5 receptors in epithelial cells can cause vasorelaxation and activation of M1 or M3 receptors in vascular smooth muscle cells can cause vasoconstriction [(Beny J L, Nguyen M N, Marino M, Matsui M (2008) Muscarinic receptor knockout mice confirm involvement of M3 receptor in endothelium-dependent vasodilatation in mouse arteries. *J Cardiovasc Pharmacol* 51, 505)]. It clearly implies that the muscarinic receptor agonist or antagonist has major effect in regulation of cardiovascular function and can be used to treat related pathophysiological conditions. The vasodilation can be effectively treated by antagonist such as 4-DAMP and M1-antagonist piperazine or M2/M4 antagonist AF-DX 11X AND AQ-RA 741[(Hendriks M G C, Pfaffendorf M, van Zwieten P A.

Characterization of the muscarinic receptor subtype mediating vasodilation in the rat perfused mesenteric vascular bed preparation. *J Auton Pharmacol* 1992; 12, 411)]. It has been shown that the bradycardia-hypotension syndrome could be treated by moderately M2 selective antagonist AF-DX 116 which protects heart against life-threatening tachyarrhythmia's associated with hypotension and bradycardia by reducing myocardial perfusion [(Mark H, Schweitzer P. Cardiovascular indications for atropine. In: Gould L A, ed. *Drug Treatment of Cardiac Arrhythmias*. Mt. Kisio, N.Y.: Futura, 1983, 377)].

Almost all isoforms of muscarinic receptors are also expressed in mammalian central nervous system. Interestingly, unique distribution pattern of different muscarinic receptors in the brain circuit involved in cognition have been shown [(van der Zee E A, Keijser J N (2011) Localization of pre- and postsynaptic cholinergic markers in rodent forebrain: a brief history and comparison of rat and mouse. *Behav Brain Res* 221, 356)]. The M1 receptor is most expressed in cortex, hippocampus and striatum, whereas the M2 receptors are found in nucleus basalis and occipital cortex. M3 receptors are expressed in substantially lower concentration with similar cortical distribution to that of M1 receptor, while the M4 receptors are mainly found in striatum, caudate putamen and at lesser degree in hippocampus. The M5 receptors are expressed in much lower concentration hippocampus and ventral tegmental area [(Carruthers S P, Gurvich C T, Rossell S L, The muscarinic system, cognition and schizophrenia, *Neurosci Biobehav Rev.* 2015 August; 55, 393)].

Muscarinic receptor antagonist are known to produce impairments in attention learning and memory, whereas agonist show cognition enhancement such as improvement in normal cognition function or reversal of effect induced by muscarinic receptor antagonist and attenuation of cognitive deficit in neurological or psychiatric disorders such as Alzheimer's Disease and Schizophrenia [(Green A, Ellis K A, Ellis J, Bartholomeusz C F, Ilic S, Croft R J, Phan K L, Nathan P J (2005) Muscarinic and nicotinic receptor modulation of object and spatial n-back working memory in humans. *Pharmacol Biochem Behav* 81, 575)]. These observations suggest that selective agonist of muscarinic receptor could be used for effective treatment for various cognitive impairments associated with neurological and psychiatric disorders such as Alzheimer's disease, schizophrenia and dementia. Importantly, the M2/M4 receptor are orthosteric agonist xanomeline administration which improves cognitive function and reduce the severity of psychotic symptoms in patients with Alzheimer's disease. Moreover in animal models of schizophrenia the xanomeline was found to exhibit nootropic and antipsychotic drug-like qualities [(Veroff, A. E., Bodick, N.C., Offen, W. W., Sramek, J. J., Cutler, N. R., 1998.

Efficacy of xanomeline in Alzheimer disease: cognitive improvement measured using the computerized neuropsychological test battery (CNTB). *Alzheimer Dis. Assoc. Dis.* 12 (4), 304); (Shekhar, A., Potter, W. Z., Lightfoot, J., Lienemann, J., Dub6, S., Mallinckrodt, C., et al., 2008, Selective muscarinic receptor agonist xanomeline as a novel treatment approach for schizophrenia. *Am. J. Psychiatry* 165 (8), 1033)]

M2 receptor antagonist increases level of acetylcholine and increase scholinergic transmission by blocking auto receptor function. This results in the improvement of cognition with decreased chances of cholinergic side effects. The piperazine based M2 receptor antagonist SCH 57790 which has sufficient selectivity for M2 display activity in various animal models of cognition and has potential in treatment of AD [(Carey G J, Billard W, Binch H, Cohen-Williams M, Crosby G, Grzelak M, et al. SCH 57790, a selective muscarinic M2 receptor antagonist, releases acetylcholine and produces cognitive enhancement in laboratory animals. *Eur J Pharmacol* 2001; 431(2), 189)]. Moreover, the central muscarinic-cholinergic system, more specifically M2 receptors are also implicated in the pathogenesis of depressive symptoms depressive disorders [(Brian Dean, Cholinergic muscarinic receptors: new opportunities to treat psychiatric disorders, *Future Med. Chem.* 2013, 5(13), 1547)].

US patent publication US2014148420 reports that antagonism of M3 muscarinic receptor by novel compound 3(R)-(2-hydroxy-2,2-dithien-2-ylacetoxy)-1-(3-phenoxypropyl)-1-azoniablcyclo[2.2.2]octane, can be used in treatment of respiratory disease, e.g., asthma or chronic obstructive pulmonary diseases.

PCT application WO2014014698 discloses bitopic muscarinic antagonist named JB-D4 which may be used as neuromuscular blocking agents (e.g., for use in compositions for anesthetizing a subject) and for the treatment of central nervous system disorders (e.g., Parkinson's disease, Schizophrenia, etc.), Overactive Bladder Syndrome, Chronic Obstructive Pulmonary Disease, asthma, and many other diseases associated with the activation or inhibition of M1-M5 acetylcholine receptors.

The Chinese patent publication CN103242214 describes process for preparation of novel indole derivatives which can be used to treat IBS, dysuria and COPD. Moreover, patent publication CN103502213 and US2013196978 by Chiesi reports process for preparation of alkaloid esters and carbamate derivatives for treatment of asthma, COPD or inflammatory diseases.

PCT application by Dainippon Sumitomo Pharma WO 2013122107 discloses novel fused-ring pyrrolidine derivatives for treating various diseased mediated by mAChRs.

PCT application WO2014045031 by Heptares Therapeutics reports novel bicyclic aza compounds which are M1 receptor agonist, which are useful for treating cognitive or psychotic disorders or for treating or lessening the severity of acute, chronic, neuropathic or inflammatory pain.

The US patent US 2013225624 by IIBR discloses novel bicyclic spiro compounds which are M1 receptor modulators and are useful for treating neurodegenerative diseases, learning and memory process or for neuroprotection.

PCT applications WO 2014035829, WO 2013126856, WO 2013106795 and WO2013103931 by Vanderbilt University reports novel compounds substituted aminothieno[2,3-c]pyridine-2-carboxamide analogues, substituted 4-(1H-pyrazol-4-yl)-benzyl analogues, substituted 1-benzylindolin-2-one analogues that modulated M1 receptor and useful for treating various neurological and psychiatric disorders.

The US patent US 2013331364, US 2014051864 and US 2013267706 by Theravance discloses diamide compounds, quaternary ammonium diphenylmethyl compounds, guanidine-containing compounds, respectively, that are mAChR antagonists which are useful for treating pulmonary diseases.

PCT application WO0107406 by Banyu Pharm Co Ltd discloses various M3 receptor antagonists for treatment of COPD and urinary incontinence.

Majority of muscarinic receptor modulators are very non-selective, hence the design, synthesis and development of new muscarinic receptor agonist or antagonist with greater selectivity is urgently required for treatment of various pathophysiological conditions such as COPD, PH, cardiovascular dysfunction, cognition, learning and memory, mood disorder and ADHD.

Absence of selective M2 muscarinic receptor agonist hampered the characterization of M2 receptor for exploring its therapeutic potential in pathogenic conditions such as Alzheimer's disease, schizophrenia, etc. Milameline is one such a non-selective muscarinic receptor agonist which was under clinical trial for treatment of Alzheimer's disease.

However, the further drug development has halted due to poor results in clinical trial. (Sedman A J, Bockbrader H, Schwarz R D (1995). Preclinical and phase 1 clinical characterization of CI-979/RU35926, a novel muscarinic agonist for the treatment of Alzheirners disease, *Life Sciences,* 56 (11-12): 877-82). Moreover, several different muscarinic agonist tested in patients with Senile dementia-Alzheimer type (SDAT) such as arecoline, bathanechol, pilocarpine and RS-86 have shown mixed results. (R. D. SCHWARZ, M. J. CALLAHAN, R. E. DAVIS, J. C. JAEN, W. LIPINSKI, C. RABY, C. J. SPENCER, AND H. TECLE. Alzheimer Disease: Therapeutic Strategies. R. Becker and E. Giacobini (eds.), Birkhauser, Boston (1994)).

M3 muscarinic receptor antagonist are useful in treatment of various disorders associated with COPD (chronic obstructive pulmonary disease), OAB (overactive bladder), obesity, etc. (Andrew C. Kruse, Brian K. Kobilka, Dinesh Gautam, Patrick M. Sexton, Arthur Christopoulos & Jiirgen Wess, Muscarinic acetylcholine receptors: novel opportunities for drug development, *Nature Reviews Drug Discovery,* 13, 549-560 (2014)). Aclidinium bromide is compound used for the treatment of COPD, with IC50-0.14 nM against M3 muscarinic receptor. However it is very non selective and hence displays several side effects. Similarly, atropine, hyoscyamine, ipratropium, oxybutynin, tolterodine, zamifenacin are used to for treatment of various disorder associated with M3 muscarinic receptor, but all of them are non-selectivity. Darifenacin is yet another M3 muscarinic receptor antagonist which is used for treatment of OAB with IC50 activity 8.9 $pK_i$.

OBJECTS OF THE INVENTION

The main object of the invention is to provide substituted methanopyrido[2,1-a]isoindolones of formula I having selective muscarinic receptor modulators activity which are useful for the treatment of diseases where muscarinic receptors play critic role in pathophysiology, such as COPD, PH, cardiovascular dysfunction, dementia, Alzheimer's, mood disorders and ADHD.

Another object of the invention is to provide a process of synthesis for compounds of formula I.

Further object of the invention is to provide a pharmaceutical composition comprising of compounds of formula I and other suitable excipients.

SUMMARY OF THE INVENTION

Accordingly, the present invention discloses substituted methanopyrido[2,1-a]isoindolones of formula I having high activity as well as selectivity for muscarinic acetylcholine receptors,

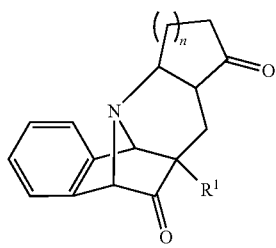

Formula I wherein, $R^1$ is selected from phenylsulfonyl or p-toluenesulfonyl; and n=1, 2, 3.

In an embodiment of the invention wherein the representative compounds of formula I comprising of but not limited to—
- (4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione and its enantiomer: (RG-02)
- (4aS,6R,6aR,11S,12aR)-methyl 4-oxo-6-(phenylsulfonyl)-1,2,3,4,4a,5,6,6a,11,12a-decahydroisoindolo[2,1-a]quinoline-11-carboxylate and its enantiomer: (RG-04)
- (4aS,6R,6aR,11S,12aR)-ethyl 4-oxo-6-(phenylsulfonyl)-1,2,3,4,4a,5,6,6a,11,12a-decahydroisoindolo[2,1-a]quinoline-11-carboxylate and its enantiomer: (RG-05)
- (4aS,6S,6aR,11S,12aR)-6-tosyl-1,2,3,4a,5,6,6a,12a-octahydro-6,11-methanoisoindolo[2,1-a]quinoline-4,13(11H)-dione and its enantiomer: (RG-06)
- ((3aR,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione and its enantiomer: (RG-09)
- (3aS,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione and its enantiomer: (RG-10)
- (6S,6aR,11S,12aR)-13-oxo-6-(phenyl sulfonyl)-1,2,3,5,6,6a,11,12a-octahydro-6,11-methanoisoindolo[2,1-a]quinolin-4-yl trifluoromethanesulfonate and its enantiomer: (RG-12)
- (6S,6aR,11S,12aR)-13-oxo-6-tosyl-1,2,3,5,6,6a,11,12a-octahydro-6,11-methanoisoindolo[2,1-a]quinolin-4-yl trifluoromethanesulfonate and its enantiomer: (RG-13)
- (−)-(4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione and its enantiomer: (RG-02)

In another embodiment of the invention wherein the compounds of formula I modulates the muscarinic receptors and hence can be used for treatment of various pathophysiological conditions associated with muscarinic receptors such as COPD, PH, cardiovascular dysfunction, dementia, Alzheimer's, mood disorders and ADHD.

In yet another embodiment of the invention wherein the process for the preparation of compounds of formula I comprising of following steps:
i. reacting compounds of formula (a) [can be prepared by procedure described in *Org. Biomol. Chem.,* 2015, 13, 4438] with the compound of formula (b)[commercially available or can be prepared by Baylis-Hillman reaction of cycloalkenone and formaldehyde followed by acetylation; the procedures are described in—Ciganek, E. Organic Reactions; John Wiley & Sons: New York, 1997; Vol. 51, pp 201-350]

formula (a)

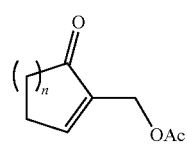

formula (b)

wherein R¹ is selected from phenylsulfonyl or p-toluenesulfonyl and n=1, 2, 3 in presence of different metal catalyst such as Pd, Cu, Rh, Ru along with various ligands such as PBu₃, PPh₃, to generate allyl carbocation of compound of formula (b) in presence of inert organic solvents such as THF, aromatic hydrocarbon such as toluene, o-, m-, p-xylene to afford the coupled product, additionally different organic or inorganic bases can be or cannot be used to promote the catalytic cycle, the inert atmosphere can be maintained by using different gases such as Ar, N₂, He, the temperature of reaction can be −20° C. to 80° C., preferably rt, the duration of reaction can be between 1-24 hrs, preferably 6 h to obtain compound of formula (c) wherein R¹ is phenylsulfonyl or p-toluenesulfonyl and n=1, 2, 3 formula (c)

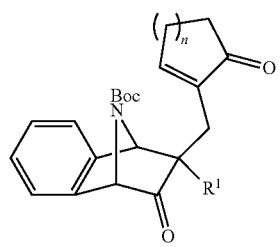

ii. reacting compound of formula (c) on deprotection followed by Michael addition by employing suitable reaction conditions, the temperature of reaction can be −20° C. to 80° C., preferably room temperature, the duration of reaction can be between 1-24 hrs, preferably 6 h to obtain compound of formula I wherein R¹ is phenylsulfonyl or p-toluenesulfonyl and n=1, 2, 3

General formula I

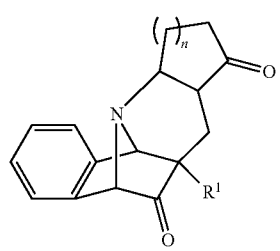

iii. conversion of compound of formula I with its corresponding enol triflate, by employing suitable reaction conditions, the temperature of reaction can be −20° C. to 80° C., preferably room temperature, the duration of reaction can be between 6-48 hrs, preferably 36 hrs obtain compounds of formula (d) wherein R¹ is phenylsulfonyl or p-toluenesulfonyl and n=1, 2, 3 formula (d)

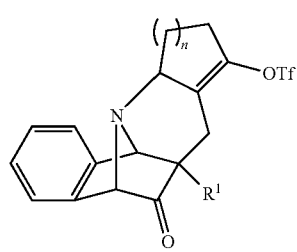

iv. reacting compound of formula I with various different nucleophile to undergo C—C bond cleavage, by employing suitable reaction conditions, the temperature of reaction can be −20° C. to 80° C., preferably room temperature, the duration of reaction can be between 6-48 hrs, preferably 12 h to obtain compounds of formula (e) wherein R¹ is phenylsulfonly or p-toluenesulfonyl; R² is alkyl, phenyl, trifluoroethyl, hydrogen and n=1, 2, 3 formula (e)

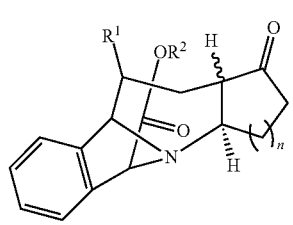

v. reacting compound of formula I with different common acids (H-A) include hydrochloric, hydrobromic, hydroiodic, nitric, sulfuric, phosphoric, hypophosphoric, trifluoroacetic, acetic and the like to obtain the corresponding salt of formula (f) wherein R¹ is phenylsulfonly or p-toluenesulfonyl; R² is alkyl, phenyl, trifluoroethyl, hydrogen and n=1, 2, 3.

formula (f)

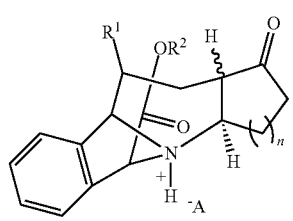

In yet another embodiment of the invention wherein a pharmaceutical composition comprising of compounds of formula I optionally along with one or more pharmaceutical excipients.

In another embodiment of the invention wherein a pharmaceutical composition optionally comprising of one or more suitable drugs (for example: RG-02 was given to mice in solution containing: 1 mg/ml of RG-02, 0.9% Sodium chloride, 5% DMSO, so the final dose of RG02 in mice was: 10 mg/kg, on the basis of 10 ml (of above formulation)/kg body wt of mice administration) (FIG. 4 and FIG. 5) which modulates muscarinic receptors such as Xanomeline, Aceclidine, Pilocarpine, Cevimeline, Oxotremorine, Atropine, Scopolamine, Hydroxyzine, Ipratropium, Tropicamide, Pirenzepine, Diphenhydramine, Doxylamine, Dimenhydrinate, Dicyclomine, Flavoxate, Oxyburynin, Titropium, Cyclopentolate, Atropine methonitrate, Trihexylphenidyl/Benzhexol, Tolterodine, Solifenacin, Darifenacin, Benzatropine, Mebeverine, Procyclidine, Aclidinium bromide, etc along with compounds of formula I to provide synergistic effect on treatment of various pathophysiological conditions associated with muscarinic receptors.

In yet another embodiment of the invention wherein method for treating or preventing various pathophysiological conditions associated with muscarinic receptors in a subject comprising of administrating an effective amount of compound of formula I together with one or more pharmaceutical carriers.

In yet another embodiment of the invention wherein use of compounds of formula I for the preparation of medicaments useful for treating or preventing pathophysiological conditions mediated by muscarinic receptors in a subject.

BRIEF DESCRIPTION OF THE DRAWINGS

The present invention may be more clearly understood by reference to the following Table/Figures.

Table 1 represents the agonist or antagonist activity of compounds at M1, M2, M3 and M5 receptor (pIC50 or pEC50 values were obtained using live cells assays as described in method sections).

ABBREVIATIONS

Figure 1:
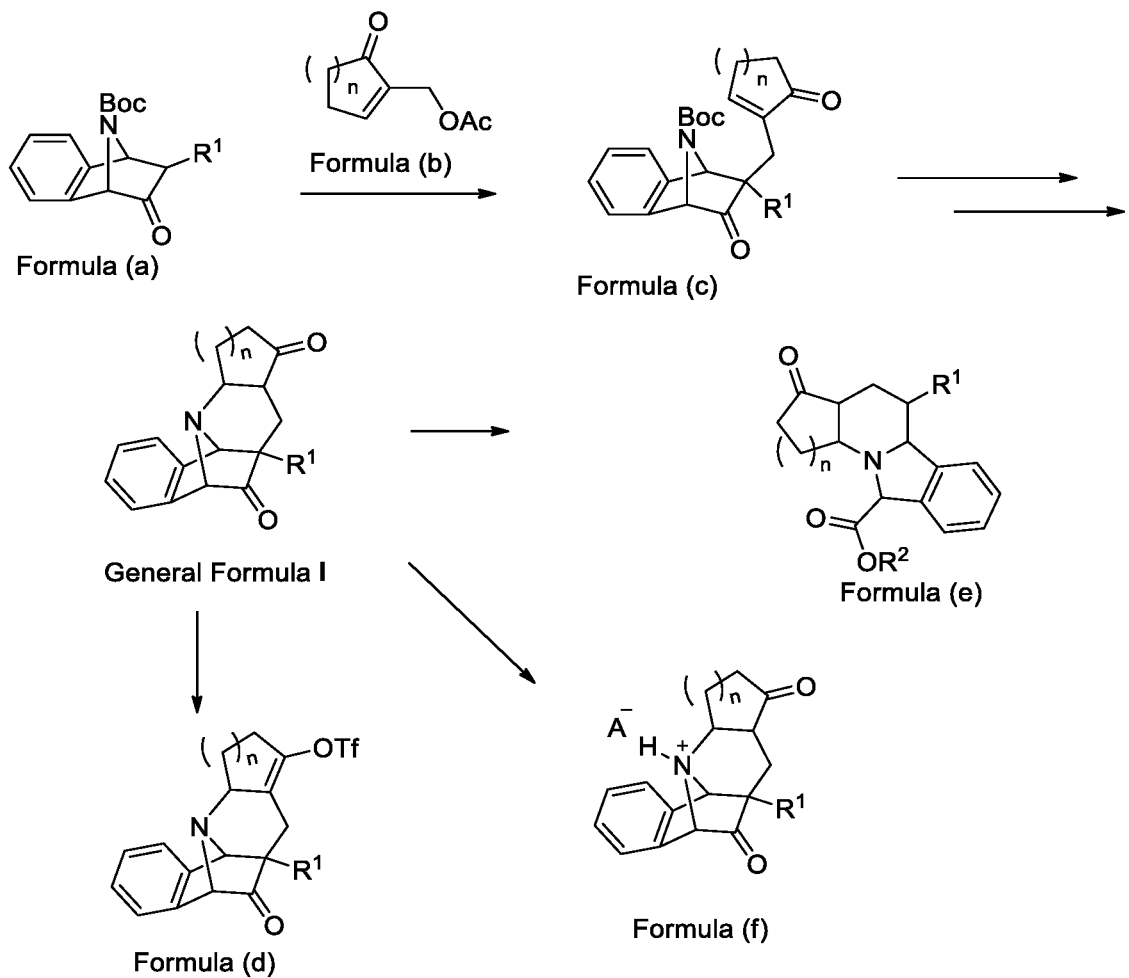
FIG. 1 illustrates the schematic pathway for the synthesis of compounds of formula I.
Figure 2:
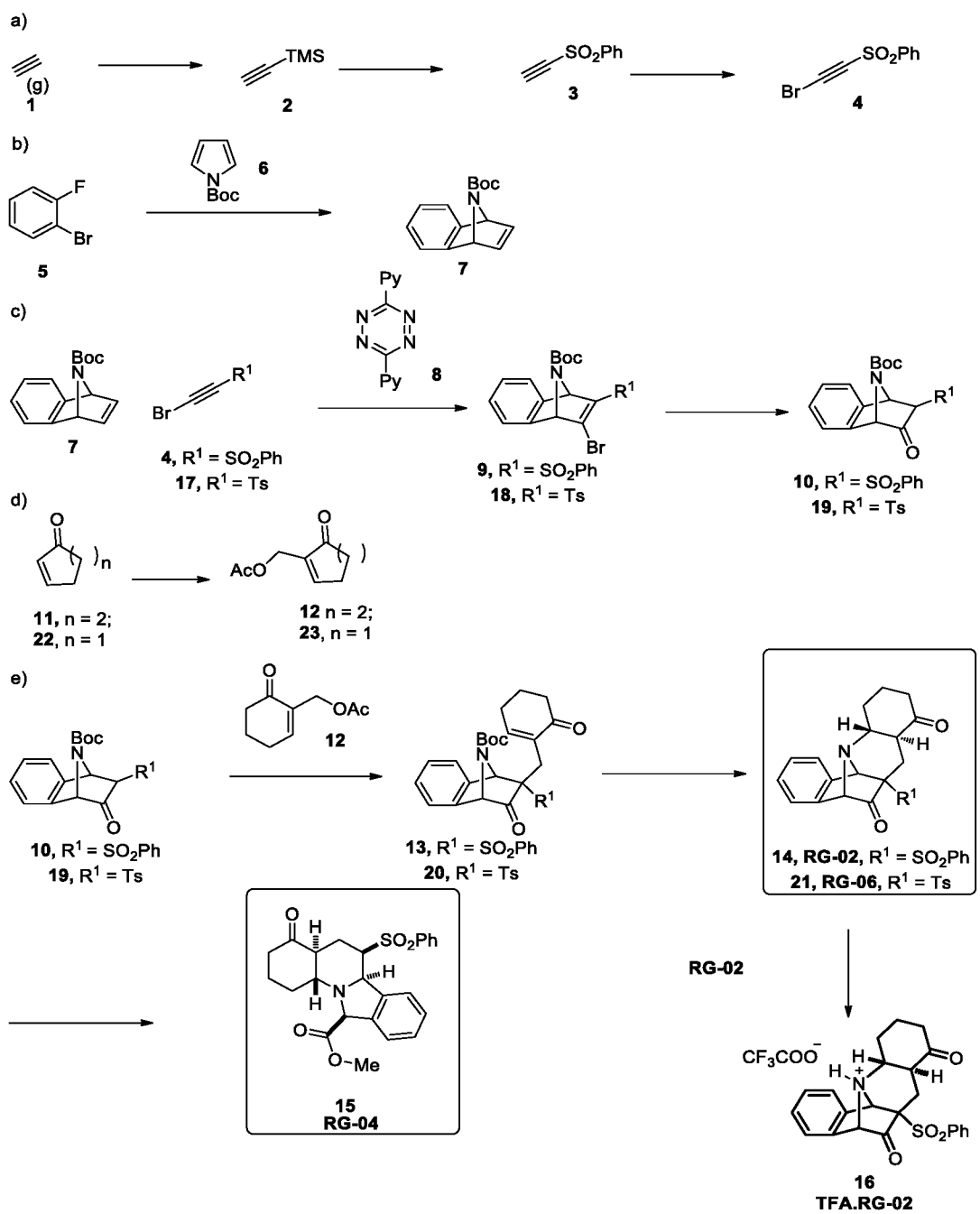
FIG. 2 illustrates the schematic pathway for the synthesis of intermediates and representative compounds RG-02 and RG-04.

ADHD attention deficit hyperactivity disorders
aq. Aqueous
bp boiling point
Bn Benzyl
Calcd Calculated
cAMP cyclic adenosine monophosphate
CNS central nervous system
COPD chronic obstructive pulmonary disease
COSY correlated spectroscopy
Cu Copper
DCM Dichloromethane
DEPT distortionless enhancement by polarization transfer
DMF N,N-dimethyl formamide
DMSO Dimethylsulfoxide
EC50 half maximal effective concentration
Esi electrospray ionization
EtOAc ethyl acetate
FSK Forskoline
g Gram
GPCRs G-protein coupled receptors
h Hour
HBSS Hank's balanced salt solution
HEPES (4-(2-hydroxyethyl)-1-piperazineethanesulfonic acid
HRMS high resolution mass spectroscopy
Hz Hertz
IC50 half maximal inhibitory concentration
IAEC institutional animal ethics committee
IC Intracutaneous
ID intradermal
IM intramuscular
IP Intraperitoneal
IV intravenous
mAChR muscarinic acetylcholine receptors
mL milliliter
MeOH methanol
mp melting point
MWM Morris water maze
NFAT nuclear factor of activated T-cells
NMR nuclear magnetic resonance
NOE nuclear overhauser effect
NOESY nuclear overhauser enhancement spectroscopy
NOR novel object recognition
OAB overactive bladder
PAH pulmonary arterial hypertension
PBu$_3$ tributylphosphine
PDC pyridinium dichromate
Pd palladium
PEI polyethyleneamine
PH pulmonary hypertension
PO oral
PPh$_3$ triphenylphosphine
p-TSA p-Toluenesulfonic acid
py pyridine
Rh rhodium
rt room temperature
Ru ruthenium
SDAT Senile dementia-Alzheimer type
SEM standard error of mean
THF tetrahydrofuran
TFA trifluoroacetic acid
TLC thin layer chromatography
TMS Trimethylsilyl

DETAILED DESCRIPTION OF THE INVENTION

The present invention discloses substituted methanopyrido[2,1-a]isoindolones of formula I

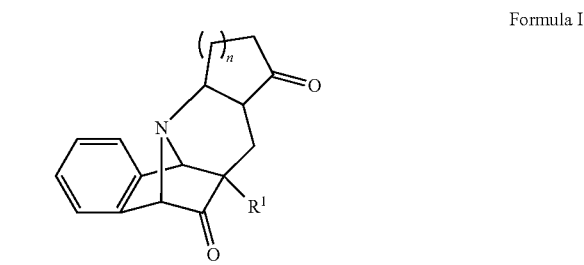

Formula I wherein R$^1$ is selected from phenylsulfonyl or p-toluenesulfonyl; and n=1, 2, 3.

The compounds of formula I according to the invention encompass an enantiomer, diastereomer, racemate, tautomer, geometrical isomers, or pharmaceutically acceptable salt thereof. The compound of formula I according to the present invention also encompasses ester and pure form thereof.

Following examples are given by way of illustration and should not be construed to limit the scope of the present invention.

(4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione and its enantiomer: (RG-02)

(4aS,6R,6aR,11S,12aR)-methyl 4-oxo-6-(phenylsulfonyl)-1,2,3,4,4a,5,6,6a,11,12a-decahydroisoindolo[2,1-a]quinoline-11-carboxylate and its enantiomer: (RG-04)

(4aS,6R,6aR,11S,12aR)-ethyl 4-oxo-6-(phenylsulfonyl)-1,2,3,4,4a,5,6,6a,11,12a-decahydroisoindolo[2,1-a]quinoline-11-carboxylate and its enantiomer: (RG-05)

(4aS,6S,6aR,11S,12aR)-6-tosyl-1,2,3,4a,5,6,6a,12a-octahydro-6,11-methanoisoindolo[2,1-a]quinoline-4,13(11H)-dione and its enantiomer: (RG-06)

(3aR,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione and its enantiomer: (RG-09)

(3aS,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione and its enantiomer: (RG-10)

(6S,6aR,11S,12aR)-13-oxo-6-(phenylsulfonyl)-1,2,3,5,6,6a,11,12a-octahydro-6,11-methanoisoindolo[2,1-a]quinolin-4-yl trifluoromethanesulfonate and its enantiomer: (RG-12)

(6S,6aR,11S,12aR)-13-oxo-6-tosyl-1,2,3,5,6,6a,11,12a-octahydro-6,11-methanoisoindolo[2,1-a]quinolin-4-yl trifluoromethanesulfonate and its enantiomer: (RG-13)

(−)-(4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione and its enantiomer: (RG-02)

SYNTHESIS

The process for the preparation of compounds of formula I comprising of following steps:

i. reacting compounds of formula (a) with the compound of formula (b) in presence of different metal catalyst such as Pd, Cu, Rh, Ru along with various ligands such as PBu$_3$, PPh$_3$, to generate allyl carbocation of compound of formula (b) in presence of inert organic solvents such as THF, aromatic hydrocarbon such as toluene, o-, m-, p-xylene to afford the coupled product, additionally different organic or inorganic bases can be or cannot be used to promote the catalytic cycle, the inert atmosphere can be maintained by using different gases such as Ar, N$_2$, He, the temperature of reaction can be −20° C. to 80° C., preferably room temperature, the duration of reaction can be between 1-24 hrs, preferably 6 h to obtain compound of formula (c).

ii. reacting compound of formula (c) on deprotection followed by Michael addition by employing suitable reaction conditions, the temperature of reaction can be −20° C. to 80° C., preferably rt, the duration of reaction can be between 1-24 hrs, preferably 6 h to obtain compound of formula I.

iii. conversion of compound of formula I with its corresponding enol triflate, by employing suitable reaction conditions, the temperature of reaction can be −20° C. to 80° C., preferably room temperature, the duration of reaction can be between 6-48 hrs, preferably 36 h to obtain compounds of formula (d).

iv. reacting compound of formula I with various different nucleophile to undergo C—C bond cleavage, by employing suitable reaction conditions, the temperature of reaction can be −20° C. to 80° C., preferably room temperature, the duration of reaction can be between 6-48 hrs, preferably 12 h to obtain compounds of formula (e).

v. reacting compound of formula I with different common acids (H-A) include hydrochloric, hydrobromic, hydroiodic, nitric, sulfuric, phosphoric, hypophosphoric, trifluoroacetic, acetic and the like to obtain the corresponding salt of formula (f) wherein R$^1$ is phenylsulfonly or p-toluenesulfonyl; R$^2$ is alkyl, phenyl, trifluoroethyl, hydrogen and n=1, 2, 3.

EXAMPLES

The following examples given by way of illustration of the working of the invention in actual practice and should not be construed to limit the scope of the present invention in any way.

Example 1: (4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione and its enantiomer (RG-02

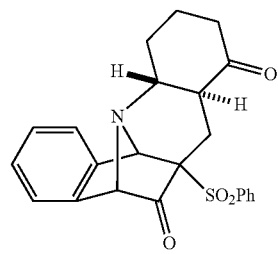

To the stirring solution of (1R,2S,4S)-tert-butyl 3-oxo-2-((6-oxocyclohex-1-en-1-yl)methyl)-2-(phenylsulfonyl)-1,2,3,4-tetrahydro-1,4-epiminonaphthalene-9-carboxylate 13 (2 g, 3.94 mmol) in 20 mL dry DCM was added trifluoroacetic acid (1.51 ml, 19.70 mmol) dropwise at 0° C. under argon and the reaction was allowed to stir for 6 h and completion of reaction was monitored by TLC in 70% EtOAc:hexane. The reaction mixture was concentrated with high vacuum to remove excess of trifluoroacetic and then dissolved in EtOAc. It was washed with 100 mL aqueous solution of NaHCO$_3$ (10%) and 100 mL×3 water. The organic layer was dried over Na$_2$SO$_4$, concentrated and purified by column chromatography with 30% EtOAc:Hexane to afford 1.3 g (81%) of RG-02 as yellowish solid. IR (KBr) $\bar{v}$=3435, 2921, 2352, 1621, 1450, 1156, 1046, 794 cm$^1$; $^1$H NMR (400 MHz, CDCl$_3$) δ 7.79 (d, J=7.4 Hz, 2H), 7.58 (dd, J=13.1, 7.0 Hz, 2H), 7.47 (t, J=7.6 Hz, 2H), 7.38 (d, J=7.2 Hz, 1H), 7.35-7.27 (m, 2H), 4.74 (s, 1H), 4.58 (s, 1H), 3.11-2.99 (m, 1H), 2.63 (td, J=12.2, 4.3 Hz, 1H), 2.42 (d, J=12.9 Hz, 1H), 2.37 (d, J=4.8 Hz, 1H), 2.24 (dd, J=13.5, 6.7 Hz, 1H), 2.09 (d, J=8.9 Hz, 2H), 2.05 (d, J=4.1 Hz, 1H), 2.02 (d, J=3.8 Hz, 1H), 1.74 (dd, J=12.4, 3.4 Hz, 1H); $^{13}$C NMR (100 MHz, CDCl$_3$) δ 206.74, 203.43, 142.19, 136.32, 135.77, 134.15, 129.95, 128.90, 128.81, 128.61, 124.24, 122.44, 71.69, 71.23, 69.69, 63.11, 51.39, 40.50, 30.27, 30.03, 23.27; HRMS (ESI) m/z 430.1078 [(M+Na)$^+$ calcd. for (C$_{23}$H$_{21}$NO$_4$SNa)$^+$: 430.1089].

Example 2: (4aS,6R,6aR,11S,12aR)-methyl 4-oxo-6-(phenylsulfonyl)-1,2,3,4,4a,5,6,6a,11,12a-decahydroisoindolo[2,1-a]quinoline-1-carboxylate and its enantiomer (RG-04

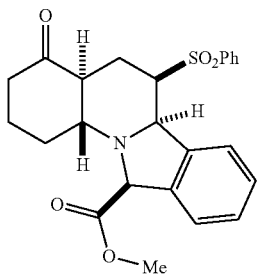

To the stirring solution of RG-02 (0.1 g, 0.24 mmol) in 2 mL MeOH was added NaOMe (14 mg, 0.269 mmol) as reaction was allowed to stir for 3 h at rt. The completion of reaction was monitored by TLC in 70% EtOAc:Hexane. The reaction mixture was concentrated, dissolved in EtOAc and extracted with water. The organic layer was dried on $Na_2SO_4$, concentrated and purified by column chromatography with 35% EtOAc:Hexane to afford the 80 mg (74%) of RG-04 as yellowish semi-solid compound. IR (KBr) $\bar{v}$=3435, 2924, 2083, 1634, 1447, 1307, 1142, 1046, 794, 753; $^1$H NMR (400 MHz, CDCl$_3$) δ8.17 (d, J=7.7 Hz, 1H), 7.90 (d, J=7.4 Hz, 2H), 7.65 (t, J=7.4 Hz, 1H), 7.57 (t, J=7.5 Hz, 2H), 7.37 (dt, J=7.9, 4.2 Hz, 1H), 7.31 (d, J=4.5 Hz, 2H), 4.98 (s, 1H), 4.55 (d, J=9.3 Hz, 1H), 4.31-4.19 (m, 2H), 3.60 (ddd, J=12.8, 9.3, 3.8 Hz, 1H), 2.94 (td, J=11.1, 3.3 Hz, 1H), 2.78 (td, J=10.9, 3.8 Hz, 1H), 2.32 (d, J=14.3 Hz, 1H), 2.25 (dd, J=13.5, 6.2 Hz, 1H), 2.17-2.07 (m, 2H), 1.86-1.78 (m, 1H), 1.77-1.70 (m, 2H), 1.34 (t, J=7.1 Hz, 3H); $^{13}$C NMR (100 MHz, CDCl$_3$) δ208.37, 174.41, 138.93, 138.31, 137.51, 133.91, 129.42, 128.90, 128.18, 128.09, 127.08, 121.87, 66.20, 65.53, 64.09, 63.20, 52.69, 51.57, 40.95, 28.96, 27.79, 23.70; HRMS (ESI) m/z 462.1342 [(M+Na)$^+$ calcd for (C$_{24}$H$_{25}$NO$_5$SNa)$^+$: 462.1351].

Example 3: (4aS,6R,6aR,11S,12aR)-ethyl 4-oxo-6-(phenylsulfonyl)-1,2,3,4,4a,5,6,6a,11,12a-decahydroisoindolo[2,1-a]quinoline-11-carboxylate and its enantiomer (RG-05

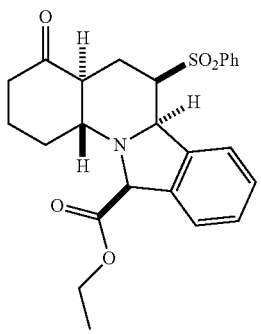

To the stirring solution of RG-02 (300 mg, 736 μmol) in 430 mmL EtOH was added NaOEt (25 mg, 368 μmol) and reaction was allowed to stir for 10 h at rt. The completion of reaction was monitored by TLC in 70% EtOAc:Hexane. The reaction mixture was concentrated, dissolved in EtOAc and extracted with water. The organic layer was dried on $Na_2SO_4$, concentrated and purified by column chromatography with 30% EtOAc:Hexane to afford the 280 mg (84%) of RG-05 as pale yellow solid compound. IR (KBr) $\bar{v}$=3435, 2926, 2092, 1642, 1302, 1138, 1052, 780, 742; $^1$H NMR (400 MHz, CDCl$_3$) δ8.17 (d, J=7.7 Hz, 1H), 7.90 (d, J=7.4 Hz, 2H), 7.65 (t, J=7.4 Hz, 1H), 7.57 (t, J=7.5 Hz, 2H), 7.37 (dt, J=7.9, 4.2 Hz, 1H), 7.31 (d, J=4.5 Hz, 2H), 4.98 (s, 1H), 4.55 (d, J=9.3 Hz, 1H), 4.31-4.19 (m, 2H), 3.60 (ddd, J=12.8, 9.3, 3.8 Hz, 1H), 2.94 (td, J=11.1, 3.3 Hz, 1H), 2.78 (td, J=10.9, 3.8 Hz, 1H), 2.32 (d, J=14.3 Hz, 1H), 2.25 (dd, J=13.5, 6.2 Hz, 1H), 2.17-2.07 (m, 2H), 1.86-1.78 (m, 1H), 1.77-1.70 (m, 2H), 1.34 (t, J=7.1 Hz, 3H); $^{13}$C NMR (100 MHz, CDCl$_3$) δ208.58, 174.03, 139.04, 138.26, 137.71, 133.89, 129.40, 128.87, 128.12, 127.95, 127.05, 121.84, 66.19, 65.26, 64.06, 63.02, 61.62, 51.50, 41.00, 28.98, 27.75, 23.74, 14.44; HRMS (ESI) m/z 476.1496 [(M+Na)$^+$ calcd for (C$_{25}$H$_{27}$NO$_5$SNa)$^+$: 476.1508].

Example 4: (4aS,6S,6aR,11S,12aR)-6-tosyl-1,2,3,4a,5,6,6a,12a-octahydro-6,11-methanoisoindolo[2,1-a]quinoline-4,13(11H)-dione and its enantiomer (RG-06

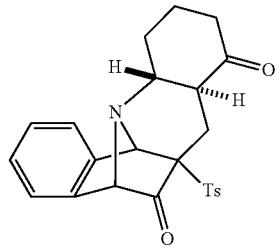 [SMILES: Cc1ccc(S(=O)(=O)C23C[C@@H]4C(=O)CCC[C@H]4N4C(C2=O)c2ccccc2C43)cc1]

To the stirring solution of (1R,2S,4S)-tert-butyl 3-oxo-2-((6-oxocyclohex-1-en-1-yl)methyl)-2-tosyl-1,2,3,4-tetrahydro-1,4-epiminonaphthalene-9-carboxylate 20 (61 mg, 362 mol) in 1 ml dry THF was added Pd(OAc)$_2$ (11 mg, 48 mol) under argon. The reaction mixture was degassed with argon for 10 min followed by dropwise addition of PBu$_3$ (48 mml, 50% sol in EtOAc, 97 mol). To this reaction mixture was added solution of tert-butyl 2-oxo-3-tosyl-1,2,3,4-tetrahydro-1,4-epiminonaphthalene-9-carboxylate in 1 ml dry THF. The reaction mixture was stirred for 8 h and the course of reaction was monitored through TLC in EtOAc:Hexane (1:1). After completion of reaction the reaction mixture was filtered through a pad of celite and concentrated. To this 2 ml dry DCM was added followed by trifluoroacetic acid (146 mml, 1.92 mmol) dropwise at 0° C. under argon and the reaction was allowed to stir for 10 h and completion of reaction was monitored by TLC in 70% EtOAc:hexane. The reaction mixture was concentrated at high vacuum to remove excess of trifluoroacetic and then dissolved in EtOAc. It was washed with 100 mL aqueous solution of NaHCO$_3$ (10%) and 100 mL×3 water. The organic layer was dried over Na$_2$SO$_4$, concentrated and purified by column chromatography with 40% EtOAc:Hexane to afford 75 mg (93%) of RG-06 as pale yellow solid. IR (KBr) $\bar{v}$=3436, 2952, 1748, 1710, 1633, 1445, 1229, 1145, 758; $^1$H NMR (400 MHz, CDCl$_3$) δ7.72-7.69 (m, 1H), 7.68-7.61 (m, 2H), 7.42-7.34 (m, 2H), 7.32-7.26 (m, 3H), 5.16-4.71 (m, 1H), 4.64-4.22 (m, 1H), 3.16 (M, 1H), 2.87-2.59 (m, 2H), 2.51 (s, 1H), 2.41 (s, 3H), 2.37 (d, J=13.6 Hz, 1H), 2.25 (d, J=7.0 Hz, 1H), 2.17-2.08 (m, 2H), 1.93-1.64 (m, 2H); $^{13}$C NMR (100 MHz, CDCl$_3$) δ206.87, 203.65, 145.34, 142.29, 135.74, 133.25, 130.04, 129.64, 128.82, 128.66, 124.28, 122.46, 77.16, 75.87, 71.74, 65.44, 63.18, 51.49, 46.89, 40.56, 34.47, 30.11, 21.78; HRMS (ESI) m/z 422.1421 [(M+H)$^+$ calcd for (C$_{24}$H$_{24}$NO$_4$S)$^+$: 422.1426], 444.1242 [(M+Na)$^+$ calcd for (C$_{24}$H$_{23}$NO$_4$SNa)$^+$: 444.1245].

Example 5: (3aR,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione and its enantiomer (RG-09

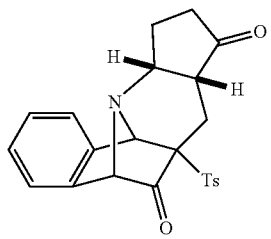 [SMILES: Cc1ccc(S(=O)(=O)C23C[C@H]4C(=O)CC[C@H]4N4C(C2=O)c2ccccc2C43)cc1]

3aS,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione and its enantiomer (RG-10

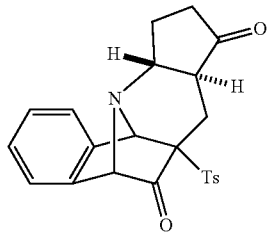 [SMILES: Cc1ccc(S(=O)(=O)C23C[C@@H]4C(=O)CC[C@H]4N4C(C2=O)c2ccccc2C43)cc1]

To the stirring solution of (5-oxocyclopent-1-en-1-yl)methyl acetate 23 (56 mg, 363 mol) in 1 ml dry THF was added Pd(OAc)$_2$ (11 mg, 48 μmol) under argon. The reaction mixture was degassed with argon for 10-15 min followed by dropwise addition of PBu$_3$ (48 mml, 50% sol in EtOAc, 97 μmol). To this reaction mixture was added solution of tert-butyl 2-oxo-3-tosyl-1,2,3,4-tetrahydro-1,4-epiminonaphthalene-9-carboxylate (100 mg, 241.85 μmol) in 1 ml dry THF. The reaction mixture was stirred for 10 h and the course of reaction was monitored through TLC in EtOAc: Hexane (1:1). After completion of reaction the reaction mixture was filtered through a pad of celite and concentrated. To this 2 ml dry DCM was added followed by trifluoroacetic acid (136 mml, 1.7 mmol) dropwise at 0° C. under argon and the reaction was allowed to stir for 10 h and completion of reaction was monitored by TLC in 70% EtOAc:hexane. The reaction mixture was concentrated at high vacuum to remove excess of trifluoroacetic and then dissolved in EtOAc. It was washed with 100 mL aqueous solution of NaHCO$_3$ (10%) and 100 mL×3 water. The organic layer was dried over Na$_2$SO$_4$, concentrated and purified by column chromatography with 35% EtOAc: Hexane to afford 30 mg (40%) of RG-09 and 32 mg (41%) of RG-10 as pale yellow solid.

Spectral Data for RG-09: IR (KBr) $\bar{v}$=3435, 2924, 1743, 1679, 1596, 1315, 1144, 1084, 731; $^1$H NMR (400 MHz, CDCl$_3$) δ7.67 (d, J=8.3 Hz, 3H), 7.38 (ddd, J=11.8, 10.8, 6.9 Hz, 3H), 7.31 (d, J=8.3 Hz, 2H), 4.84 (s, 1H), 4.47 (s, 1H), 3.74 (dd, J=15.2, 7.6 Hz, 1H), 2.56-2.47 (m, 2H), 2.45 (s, 3H), 2.40-2.29 (m, 2H), 2.29-2.21 (m, 2H), 2.15-2.06 (m, 1H); $^{13}$C NMR (100 MHz, CDCl$_3$) δ215.87, 202.73, 145.50, 141.97, 136.46, 133.18, 130.07, 129.71, 128.91, 128.79, 124.64, 122.38, 77.40, 67.90, 66.36, 58.38, 42.12, 36.68, 29.65, 26.95, 21.83; HRMS (ESI) m/z 408.1265 [(M+H)$^+$ calcd for (C$_{23}$H$_{22}$NO$_4$S)$^+$: 408.1270], 430.1087 [(M+Na)$^+$ calcd for (C$_{23}$H$_{21}$NO$_4$SNa)$^+$: 430.1089].

Spectral data for RG-10: IR (KBr) $\bar{v}$=3434, 2091, 1748, 1641, 1445, 1315, 1143, 1192, 748; $^1$H NMR (400 MHz, CDCl$_3$) δ7.65 (dd, J=7.6, 4.1 Hz, 3H), 7.35 (t, J=7.5 Hz, 2H), 7.28 (dd, J=12.1, 4.1 Hz, 3H), 4.71 (s, 1H), 4.32 (s, 1H), 4.20 (t, J=7.5 Hz, 1H), 2.40 (s, 3H), 2.37 (d, J=11.7 Hz, 3H), 2.32-2.25 (m, 2H), 2.18 (ddd, J=19.5, 16.2, 10.7 Hz, 2H); $^{13}$C NMR (100 MHz, CDCl$_3$) δ216.55, 201.29, 145.31, 142.43, 136.86, 133.36, 129.85, 129.64, 128.73, 128.63, 124.33, 122.55, 72.00, 69.69, 68.69, 57.56, 45.45, 35.61, 29.21, 24.87, 21.80; HRMS (ESI) m/z 408.1257 [(M+H)$^+$ calcd for (C$_{23}$H$_{22}$NO$_4$S)$^+$: 408.1270], 430.1084 [(M+Na)$^+$ calcd for (C$_{23}$H$_{21}$NO$_4$SNa)$^+$: 430.1089].

Example 7: (6S,6aR,11S,12aR)-13-oxo-6-(phenylsulfonyl)-1,2,3,5,6,6a,11,12a-octahydro-6,11-methanoisoindolo[2,1-a]quinolin-4-yl trifluoromethanesulfonate and its enantiomer (RG-12

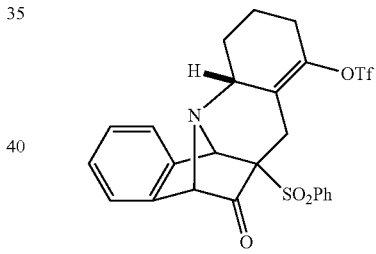

Ketone RG-02 (500 mg, 1.23 mmol), and 2,6-di-tert-butyl-4-methylpyridine (655 mg, 3.19 mmol) were dissolved in anhydrous CH$_2$Cl$_2$ (4 ml). To this solution, stirred at 0° C., triflic anhydride (412 mml, 2.45 mmol) was then added dropwise. The cloudy solution was further stirred from 0° C. to rt for 5 h. Then after hexane addition (6 ml), the formed suspension was filtered over celite.

After EtOAc rinse, the filtered solution was evaporated under reduced pressure at rt. The residue was again diluted by EtOAc (25 ml) and the solution was re-evaporated. Flash chromatography on silica gel in 30% EtOAc:Hexane affords 350 mg (52%) of RG-12 as white solid. IR (KBr) $\bar{v}$=3436, 3066, 2926, 1748, 1585, 1415, 1143, 1213, 756; $^1$H NMR (400 MHz, CDCl$_3$) δ7.83 (d, J=7.5 Hz, 2H), 7.66 (d, J=7.3 Hz, 1H), 7.64 (t, J=7.4 Hz, 1H), 7.52 (t, J=7.8 Hz, 2H), 7.41-7.35 (m, 2H), 7.32 (t, J=7.4 Hz, 1H), 5.72 (dd, J=6.4, 3.3 Hz, 1H), 4.89 (s, 1H), 4.50 (s, 1H), 3.13 (t, J=11.5 Hz, 1H), 2.79-2.73 (m, 1H), 2.36 (dd, J=9.9, 6.1 Hz, 2H), 2.18 (s, 1H), 2.17 (d, J=3.6 Hz, 1H), 2.06-2.03 (m, 1H), 1.65 (s, 1H); $^{13}$C NMR (100 MHz, CDCl$_3$) δ207.38, 173.12, 145.81, 135.99, 134.37, 130.00, 129.10, 129.07, 129.02, 128.92, 124.42, 122.68, 122.47, 119.28, 72.54, 71.74, 69.97, 60.55, 38.79, 33.18, 26.39, 23.06; HRMS (ESI) m/z 540.0753 [(M+H)+ calcd for (C$_{24}$H$_{21}$F$_3$NO$_6$S$_2$)+: 550.0762], 562.0580 [(M+Na)+ calcd for (C$_{24}$H$_{20}$F$_3$NO$_6$S$_2$Na)+: 562.0582].

Example 8: (6S,6aR,11S,12aR)-13-oxo-6-tosyl-1,2,3,5,6,6a,11,12a-octahydro-6,11-methanoisoindolo[2,1-a]quinolin-4-yl trifluoromethanesulfonate and its enantiomer (RG-13

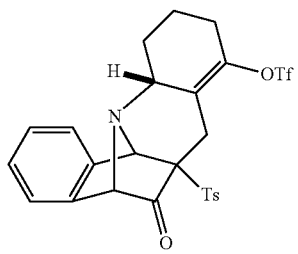 [SMILES: Cc1ccc(S(=O)(=O)C23CC4=C(OS(=O)(=O)C(F)(F)F)CCC[C@H]4N4C(C2=O)c2ccccc2C43)cc1]

Ketone RG-06 (500 mg, 1.1 mmol), and 2,6-di-tert-butyl-4-methylpyridine (633 mg, 3.08 mmol) were dissolved in anhydrous CH$_2$Cl$_2$ (4 ml). To this solution, stirred at 0° C., triflic anhydride (398 mml, 2.37 mmol) was then added dropwise. The cloudy solution was further stirred from 0° C. to rt for 8 h. Then after hexane addition (6 ml), the formed suspension was filtered over Celite. After EtOAc rinse, the filtered solution was evaporated under reduced pressure at rt. The residue was again diluted by EtOAc (25 ml) and the solution was re-evaporated. Flash chromatography on silica gel in 40% EtOAc:Hexane affords 330 mg (50%) of RG-13 as pale white solid. IR (KBr) v̄=3436, 2926, 1749, 1416, 1213, 1143, 937; $^1$H NMR (400 MHz, CDCl$_3$) δ7.67 (dd, J=18.2, 7.3 Hz, 3H), 7.43-7.26 (m, 5H), 5.81 (dd, J=70.7, 3.1 Hz, 1H), 5.11-4.81 (m, 1H), 4.50 (t, J=11.2 Hz, 1H), 3.43-3.05 (m, 1H), 2.85 (dd, J=48.4, 31.1 Hz, 2H), 2.42 (s, 3H), 2.37-2.29 (m, 2H), 2.04 (s, 1H), 1.98-1.88 (m, 1H), 1.68-1.56 (m, 1H); $^{13}$C NMR (100 MHz, CDCl$_3$) δ211.89, 145.84, 142.07, 135.72, 132.93, 130.01, 129.64, 129.03, 128.74, 124.41, 122.43, 120.02, 119.24, 100.10, 72.51, 71.74, 69.81, 65.48, 57.23, 55.81, 38.78, 26.35, 23.05; HRMS (ESI) m/z 554.0912 [(M+H)+ calcd for (C$_{25}$H$_{23}$F$_3$NO$_6$S$_2$)+: 554.0919], 576.0730 [(M+Na)+ calcd for (C$_{25}$H$_{22}$F$_3$NO$_6$S$_2$Na)+: 576.0738].

Example 9: Trifluoroacetate salt of (4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione and its enantiomer. TFA. (RG-02

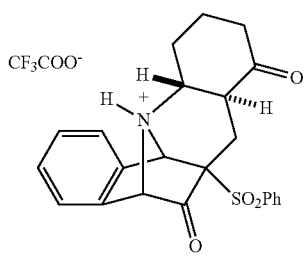

Ketone RG-02 (0.1 g, 0.25 mmol) was dissolved in 5 mL dry CH$_2$Cl$_2$ and trifluoroacetic acid (0.02 mL, 0.26 mmol) was added dropwise at 0° C. The solution was allowed to stir at room temperature for 6 hrs. The solution was evaporated under reduced pressure to afford trifluoroacetate salt of RG-02 as yellowish white solid 0.1 g (99%); IR (KBr) v̄=3562, 2927, 2368, 1820, 1765, 1628, 1458, 1117, 778 cm$^{-1}$; $^1$H NMR (400 MHz, CDCl$_3$) δ7.81, 7.79, (d, J=7.4 Hz, 2H), 7.60, 7.58 (dd, J=13.1, 7.0 Hz, 2H), 7.49, 7.47 (t, J=7.6 Hz, 2H), 7.37, 7.38 (d, J=7.2 Hz, 1H), 7.35-7.27 (m, 2H), 4.72, 4.74 (s, 1H), 4.59, 4.58 (s, 1H), 3.11-2.99 (m, 1H), 2.65, 2.63 (td, J=12.2, 4.3 Hz, 1H), 2.43, 2.42 (d, J=12.9 Hz, 1H), 2.39, 2.37 (d, J=4.8 Hz, 1H), 2.26, 2.24 (dd, J=13.5, 6.7 Hz, 1H), 2.11, 2.09 (d, J=8.9 Hz, 2H), 2.07, 2.05 (d, J=4.1 Hz, 1H), 2.05, 2.02 (d, J=3.8 Hz, 1H), 1.76, 1.74 (dd, J=12.4, 3.4 Hz, 1H); $^{13}$C NMR (100 MHz, CDCl$_3$) δ206.79, 206.74, 203.62, 203.43, 164.18, 142.49, 142.19, 136.42, 136.32, 135.91 135.77, 134.15, 133.09, 130.31 129.95, 129.25, 128.90, 128.81, 128.71, 128.61, 128.52, 125.01, 124.24, 122.53, 122.44, 116.58, 71.92, 71.69, 71.23, 70.89, 69.69, 68.95, 63.11, 62.85, 51.39, 51.21 40.50, 39.85, 31.91, 30.27, 30.03, 29.05 23.27 23.17; HRMS (ESI) m/z 408.1758 [(M+H)+ calcd. for (C$_{23}$H$_{21}$NO$_4$SNa)+: 408.1270].

Example 10: (−)-(4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione (RG-02

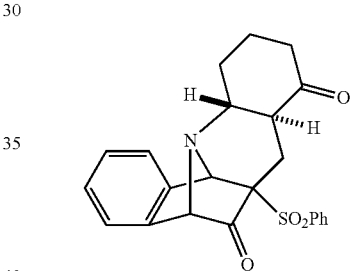

To the stirring solution of (−)-(1R,2S,4S)-tert-butyl 3-oxo-2-((6-oxocyclohex-1-en-1-yl)methyl)-2-(phenylsulfonyl)-1,2,3,4-tetrahydro-1,4-epiminonaphthalene-9-carboxylate 13 (2 g, 3.94 mmol) in 20 mL dry DCM was added trifluoroacetic acid (1.51 ml, 19.70 mmol) dropwise at 0° C. under argon and the reaction was allowed to stir for 6 h and completion of reaction was monitored by TLC in 70% EtOAc:hexane. The reaction mixture was concentrated with high vacuum to remove excess of trifluoroacetic and then dissolved in EtOAc. It was washed with 100 mL aqueous solution of NaHCO$_3$ (10%) and 100 mL×3 water. The organic layer was dried over Na$_2$SO$_4$, concentrated and purified by column chromatography with 30% EtOAc: Hexane to afford 1.3 g (81%) of (−)-RG-02 as yellowish solid. IR (KBr) v̄=3435, 2921, 2352, 1621, 1450, 1156, 1046, 794 cm$^{-1}$; $^1$H NMR (400 MHz, CDCl$_3$) δ 7.79 (d, J=7.4 Hz, 2H), 7.58 (dd, J=13.1, 7.0 Hz, 2H), 7.47 (t, J=7.6 Hz, 2H), 7.38 (d, J=7.2 Hz, 1H), 7.35-7.27 (m, 2H), 4.74 (s, 1H), 4.58 (s, 1H), 3.11-2.99 (m, 1H), 2.63 (td, J=12.2, 4.3 Hz, 1H), 2.42 (d, J=12.9 Hz, 1H), 2.37 (d, J=4.8 Hz, 1H), 2.24 (dd, J=13.5, 6.7 Hz, 1H), 2.09 (d, J=8.9 Hz, 2H), 2.05 (d, J=4.1 Hz, 1H), 2.02 (d, J=3.8 Hz, 1H), 1.74 (dd, J=12.4, 3.4 Hz, 1H); $^{13}$C NMR (100 MHz, CDCl$_3$) δ 206.74, 203.43, 142.19, 136.32, 135.77, 134.15, 129.95, 128.90, 128.61, 124.24, 122.44, 71.69, 71.23, 69.69, 63.11, 51.39, 40.50, 30.27, 30.03, 23.27; HRMS (ESI) m/z 430.1078

[(M+Na)⁺ calcd. for $(C_{23}H_{21}NO_4SNa)^+$: 430.1089]HPLC: CHIRALPAK AS-H column at 254 nm (hexane-isopropanol=60:40, flow rate 1.5 mL min-1), $t_{minor}$=3.5 min, $t_{major}$=4.3 min, ee>99%$[\alpha]_D^{21}$=−124.4 (c=1, $CH_2Cl_2$).

Although specific reagent, starting material, reaction conditions are mentioned in the FIG. 11, other related reagent/starting material can be easily substituted depending on substrate and/or reaction conditions.

The invention provides pharmaceutically acceptable compounds of the formula I for example organic or inorganic salts. The pharmaceutically acceptable acid(s) and base addition salts of compounds of formula I encompasses wide variety of organic and inorganic acids and bases and include but not limited to the physiologically acceptable salts which are often used in pharmaceutical industry. Such salts are also part of this invention. Typical inorganic acids used to form such salts include hydrochloric, hydrobromic, hydroiodic, nitric, sulfuric, phosphoric, hypophosphoric, trifluoroacetic, acetic and the like. Salts derivatives from organic acids such as aliphatic mono and dicarboxylic acid, phenyl substituted alkanoic acids hydroxyalkanoic and hydroxyalandioic acids, aromatic acids, aliphatic and aromatic sulfonic acids may also be used. Such pharmaceutically acceptable salts thus include acetate, phenylacetate, trifluoroacetate, ascorbate, benzoate, hydroxybenzoate, methoxybenzoate, methylbenzoate, cinnamate, citrate, formate, fumarate, glycollate, lactate, malate, maleate hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, sulfate, bisulfate, pyrosulfate, sulphite, bisulfate, sulfonate, benzenesulfonate, ethanesulfonate, 2-hydroxyethanesulfonate, methanesulfonate, p-toluenesulfonate, tartrate and the like.

The invention provides pharmaceutical composition (for example: RG-02 was given to mice in solution containing: 1 mg/ml of RG-02, 0.9% Sodium chloride, 5% DMSO, so the final dose of RG-02 in mice was: 10 mg/kg, on the basis of 10 ml (of above formulation)/kg body wt of mice administration) (FIG. 4 and FIG. 5) comprising a compound selected from the formula I optionally further comprising at least one pharmaceutically acceptable excipient, carrier, or diluent. The pharmaceutical compositions may optionally comprise, in addition to a compound selected from the formula I, one or more suitable drugs or known muscarinic receptor agonist/antagonist such as Xanomeline, Aceclidine, Pilocarpine, Cevimeline, Oxotremorine, Atropine, Scopolamine, Hydroxyzine, Ipratropium, Tropicamide, Pirenzepine, Diphenhydramine, Doxylamine, Dimenhydrinate, Dicyclomine, Flavoxate, Oxyburynin, Titropium, Cyclopentolate, Atropine methonitrate, Trihexylphenidyl/Benzhexol, Tolterodine, Solifenacin, Darifenacin, Benzatropine, Mebeverine, Procyclidine, Aclidinium bromide.

The pharmaceutical compositions of the present invention may be in any form which allows for the composition to be administrated to a subject. For example, the composition may be in the form of a solid, liquid or gas (aerosol). Typical routes of administration include, without limitation, topical, parenteral, transdermal, intraperitoneal (IP), intravenous (IV), oral (PO), intramuscular (IM), intracutaneous (IC), intradermal (ID), intrauterine and intrarectal. The term parenteral as used here in includes subcutaneous injections, intravenous, intramuscular, intrasternal injection or infusion techniques. Pharmaceutical compositions of the invention are formulated so as to allow the active ingredients contained therein to be bioavailable upon administration of the composition to a subject.

The solid dosage form may be formulated as tablets, pellets, capsules having different release pattern such as immediate, sustained, controlled, modified and delayed release profiles. The dosage forms may be prepared in conventional manner using specific excipients to achieve desired dosage form and release profile. It will be obvious to those of ordinary skill in the art that the optimal dosage of the active ingredient(s) in the pharmaceutical composition(s) will depend on a variety of factors including the type of subject, the particular form of the active ingredient, the manner of administration, severity of the disease and the dosage form employed.

Figure 4:
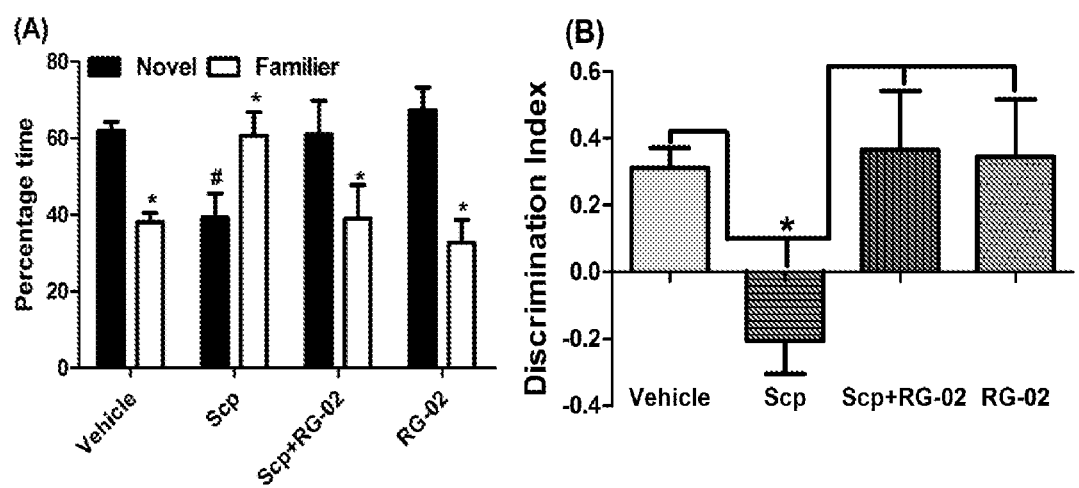
FIG. 4 illustrates the novel object recognition test indicating that Scopolamine induced memory deficit is restored by RG-02 after 7$^{th}$ day of sub chronic treatment
  A. Percent time exploration for novel object was significantly increased in Scopolamine+RG-02 group compared to Scopol amine group.
  B. Novel object discrimination index of Scopolamine+RG-02 was significantly increased as compared to Scopolamine alone group.
Each error bar represents mean±SEM (*p<0.05, n=6-9)
Figure 5:
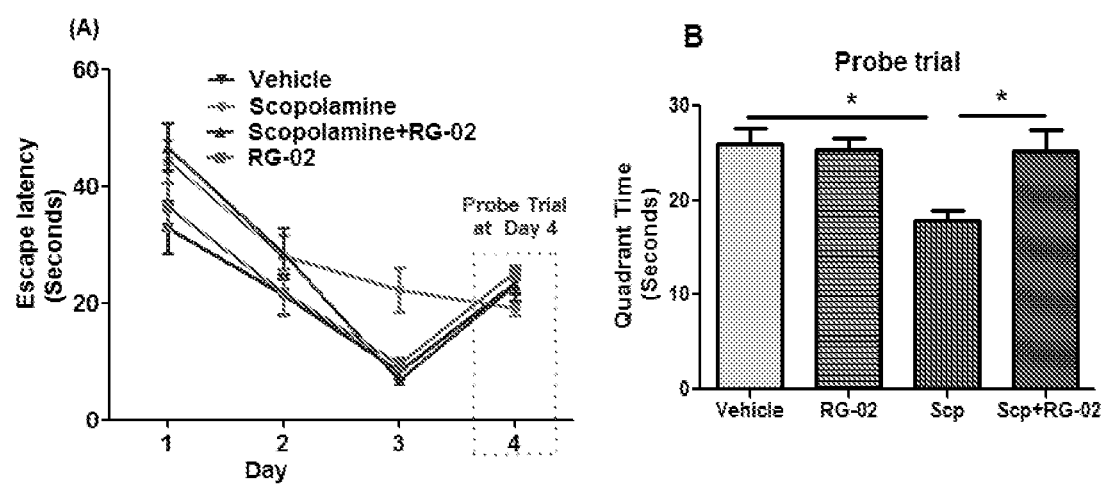
FIG. 5 illustrates the Morris Water test indicating Scopolamine induced memory deficit is restored by RG-02 after 15$^{th}$ day sub-chronic treatment of RG-02.
  A. Latency to the platform was significantly increased in Scopolamine+RG-02 group compared to scopolamine group on day 3.
  B. On day 4, time spent in platform quadrant of Scopolamine+RG-02 was significantly increased compared to Scopolamine alone group.
Each error bar represents mean SEM (*p<0.05, n=6-9).

Generally, the quantity of active compound will range between 0.5% to 90% by weight of the composition. Normally the effective amount of dosage of active compound will be in the range of 0.1 to about 100 mg/kg, more preferably about 1.0 to about 50 mg/kg of body weight/day. (FIGS. 4&5)

Moreover, the invention provides method of modulating muscarinic receptors in a mammal, comprising administrating to the said mammal in need thereof an effective amount of compound of formula I. The quantity of compound of formula I used in pharmaceutical composition of the present invention will vary depending upon the body weight of the patient and mode of administration can be of any effective amount to achieve the desired therapeutic effect. The compound of the present invention can also be administered optionally with other actives depending on the disease conditions.

Biological Activity

The compounds of formula I have stronger affinity towards muscarinic receptors and modulate their property for the potential therapeutic use.

Example 9: Agonist or Antagonist Activity of Synthesized Compounds at M1, M2, M3 and M5

First evaluation was done for all the compounds at M2 muscarinic receptor using GloSensor assay that measures the formation of cAMP in live cells expressing the human M2 receptor and a cAMP sensor. As per the analysis of the data obtained, it was concluded that the compound RG-02 is most potent agonist at M2 receptor with $pIC_{50}$ of 8.38 (IC50=4 nM), among all the compound synthesized. Also It was observed that compound RG-04 and RG-05 are also agonist at M2 receptor, but have very modest pIC50 (Table 2). Furthermore, it was found that 3 compounds RG-06, RG-12 and RG-13 are high affinity antagonist at M3 receptor with pIC50 of 9.89, 9.99 and 9.97, respectively. In addition, RG-13 compound also acts as antagonist at M1 receptor, but have very modest affinity (IC50≤1 μM). It was found that compound RG-12 acts as antagonist at more than one muscarinic receptor such as M1, M3 and M5, but exhibit very modest activity. In summary, on the basis of in vitro profiling of these compounds at muscarinic receptors, one compound RG-02 as a high affinity agonist of M2 receptor and three compounds (RG-06, RG-09 and RG-13) as high affinity antagonist of M3 receptor, were developed.

TABLE 1

Pharmacological profiling data of active molecules against mAChRs

| Compound Code No. | Compound | pIC50/pEC50 (Mean ± SEM) | | | | |
|---|---|---|---|---|---|---|
| | | M1 | M2 | M3 | M4 | M5 |
| RG-02 | | N.A. | 8.38 ± 0.35 (agonist) | N.A. | N.A. | N.A. |
| RG-04 | | N.A. | 6.247 ± 0.32 (agonist) | N.A. | N.A. | N.A. |
| RG-05 | | N.A. | 5.665 ± 0.32 (agonist) | N.A. | N.A. | N.A. |
| RG-06 | | N.A. | N.A. | 9.89 ± 0.182 (antagonist) | N.A. | N.A. |
| RG-09 | | N.A. | N.A. | 9.99 ± 0.124 (antagonist) | N.A. | N.A. |

TABLE 1-continued

Pharmacological profiling data of active molecules against mAChRs

| Compound Code No. | Compound | pIC50/pEC50 (Mean ± SEM) | | | | |
|---|---|---|---|---|---|---|
| | | M1 | M2 | M3 | M4 | M5 |
| RG-10 | [structure] | N.A. | N.A. | N.A. | N.A. | N.A. |
| RG-12 | [structure] | 6.89 ± 0.25 (antagonist) | N.A. | 5.5 ± 0.318 (antagonist) | N.A. | 6.57 ± 0.26 (antagonist) |
| RG-13 | [structure] | 6.06 ± 0.22 (antagonist) | N.A. | 9.97 ± 0.21 (antagonist) | N.A. | N.A. |
| (−)-RG-02 | [structure] | N.A. | 8.38 ± 0.35 (agonist) | N.A. | N.A. | N.A. |

N.A. (not active)

Figure 3:
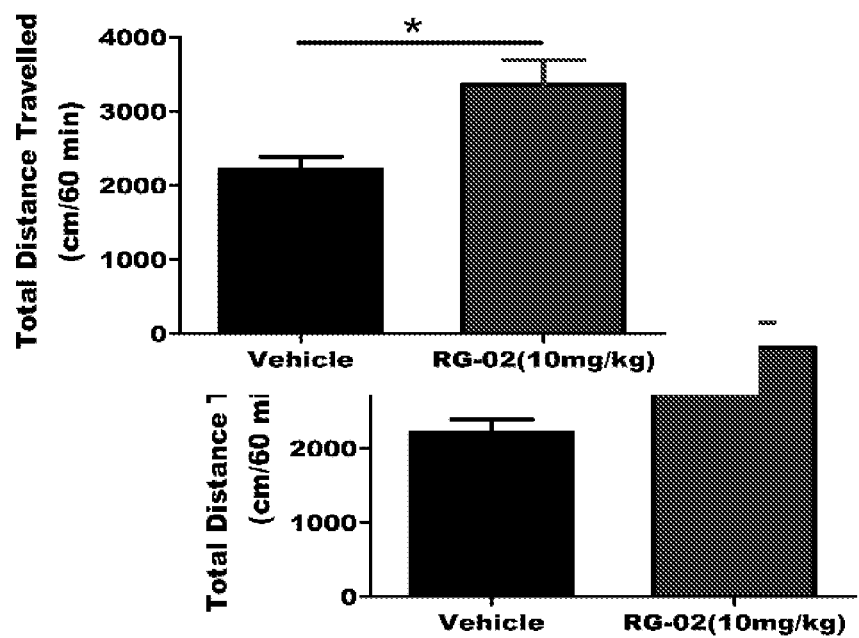
FIG. 3 illustrates the significant increase in locomotor activity in mice by acute RG-02 (10 mg/kg) treatment [*p<0.05, paired t-test analysis (n=9/group) and each error bar represents mean±SEM].

FIG. 3: Beneficial Effect of RG-02 on Exploratory Behaviour:

To determine the effect of RG-02 on mice on normal locomotor activity, the C57BL/6 mice were injected with either RG-02 (10 mg/kg; i.p.) or normal saline solution as a vehicle control after initial 30 minutes of exploration in open field arena. We measured the locomotor activity (total horizontal distance travelled in centimeter) for total 60 minutes following injection of RG-02 or vehicle. Our results as shown in figure-1 clearly depicts that RG-02 significantly increased locomotor activity compared to vehicle treated mice (p<0.05, paired student's t-test; n=9 mice/group). These results provide a proof that RG-02 has modest neurostimulatory effects in mice.

FIG. 4: RG-02 Blocks Scopolamine Induced Learning and Memory Deficits in Mice:

After treatment of RG-02 and scopolamine for six days, novel object recognition test was performed on seventh day. As expected, vehicle treated animals showed increased preference for the novel objects as compare to familiar object. In contrast, scopolamine treated animals showed marked reduction in the exploration time for the novel object as compared to vehicle treated group (p<0.05, n=6-9/group), suggesting declarative memory impairment. Importantly, co-treatment of mice with RG-02 along with scopolamine showed similar exploration time as vehicle treated mice, suggesting that RG-02 clearly blocked the deleterious effect of scopolamine treatment on memory. On the basis of the time spent in exploring novel as well as familiar objects, object discrimination index was calculated as described in method section. As expected, we found that RG-02 significantly blocked the negative effect of scopolamine on novel object discrimination (p<0.05 by ONE way ANOVA followed by Newman's Keul's post hoc analysis for multiple comparisons).

FIG. 5: Activation of M2 Receptor by RG-02 Reverses the Scopolamine Induced Learning Deficit in Morris Water Maze Test:

Since scopolamine, pan muscarinic receptor antagonist, is well established memory impairing drug, we further evaluated the effect of RG-02 (M2 receptor agonist) in scopolamine mediated of impairment of learning and memory in Morris water maze test, a well-established assay system for spatial temporal learning and memory. As shown in FIG. 3, scopolamine treated mice showed increased latency to reach the platform even on Day-3 suggesting a learning impairment in this group of animals. Interestingly, RG-02 treated mice learn the location of hidden platform just like vehicle treated mice, suggesting no per se effect of RG-02 on leaning. More importantly, RG-02 co-treatment with scopolamine prevented the scopolamine induced increased latency in MWM test. Moreover, during probe trial, scopolamine treated animals spent lesser time in quadrant with platform as compared to vehicle or RG-02 treated animals. Importantly, co treatment of RG-02 along with scopolamine increased the time spent in the quadrant with platform.

Methods

Determination of Muscarinic Receptor Specific Activity of Compound Series:

Following two assays were used to measure receptor specific activates.

1. GloSensorassay:

To measure M2 muscarinic receptor induced ($G_i$-mediated) cAMP inhibition, HEK-293T cells (procured from NCCS, Pune) were co-transfected with human M2R and luciferase based cAMP biosensor (pGloSensor™-22F plasmid; Promega) using PEImax method of transfection in the ratio of 1:1. The transfected cells were incubated at 37° C. in tissue culture incubator with 5% $CO_2$ for 14-16 hours. For GloSensor cAMP assay, after overnight incubation, media from the plate was aspirated and 100 µl of sodium luciferin solution in drug buffer (1×HBSS (pH7.4) and 20 mM HEPES) was added to the cell plates. The plates were then incubated at 37° C. in tissue culture incubator with 5% $CO_2$ for 90 minutes. After incubation, cells were treated with 20 µl of 6× diluted standard carbamoyl choline (10000 nM to 0.01 nM) along with test compounds (in triplicates) and were incubated in a humidified tissue culture incubator at 37° C. with 5% $CO_2$ for 10-15 minutes to get a steady state condition. Ligand incubation was followed by addition of 20 µl of 7×(70 µM) forskoline (FSK) to the plate. FSK incubation was followed by incubation at 37° C. for 10-15 minutes and measurement of luminescence per well using luminescence plate reader (BMG Labtech). The results were plotted as inhibition of FSK stimulated cAMP response (relative luminescence units) using nonlinear regression analysis by Graph-Pad prism V.

2. NFAT Assay:

To measure the agonist or antagonist activity at M1, M3 and M5 muscarinic receptor, NFAT-luciferase activity was performed in HEK-293T cells (procured from NCCS, Pune) by co-transfecting with human M1R or M3R or M5R and pGL4.30 (luc2P/NFAT-RE/Hygro; Promega Corp,) in 96 well format. The transfected cells were incubated at 37° C. in tissue culture incubator with 5% $CO_2$ for 14-16 hours. To determine the if the test compounds are agonist, the transfected cells were treated with either 20 µl/well of carbamoyl choline (as a positive control) at various concentrations (10000 nM to 0.01 nM) or with various concentrations of test compounds (in triplicates) and were further incubated for 12 hrs in a humidified tissue culture incubator at 37° C. with 5% $CO_2$. For antagonist mode assay, test compound incubation was followed by addition of 20 µl of 7 µM carbamoylcholine (agonist) to the plate. Following 12-14 hrs of drug treatment, media from the plate was aspirated and 100 µl of sodium luciferin solution (10 mg/ml) was added and luminescence per well was recorded using luminescence plate reader (BMG Labtech).

Behavioral Tests in Mice:

All animal experiments and procedures were executed in accordance with the guidelines established in the guide for the care and use of laboratory animals and were approved by the institutional animal ethics committee (IAEC) of CSIR-Central Drug Research Institute, Lucknow, India. In this study, male C57BL/6J mice (6-8 weeks old) weighing 22-25 g were used. They were housed on a 12-h light/dark cycle (lights on at 8.00 am) and food and water were provided ad libitum. Animals were acclimatized to the experimental room 30 minutes prior to the beginning of behavioral procedures. For experimental purpose, animals were randomly divided into four groups: vehicle, RG-02, scopolamine and scopolamine along with RG-02. In scopolamine along with RG-02 group, RG-02 (10 mg/kg, i.p) was injected thirty minutes prior to the scopolamine (0.5 mg/kg, i.p.) injections.

Locomotor Activity:

Locomotor activity was tested according to the previously published protocol (Kelly et al, 1998) with slight modifications. Briefly, mice were put in the centre of a clear Plexiglas (40×40×30 cm) open-field arena and were allowed to explore the entire arena for 30 minutes. After 30 minutes of exploration, animals were injected with either RG-02 (10 mg/kg; i.p.) or 0.9% normal saline and were allowed to explore the arena for further 60 minutes.

The animals were removed from the arena after 60 minutes of testing period and the whole arenas was cleaned with water and smell-free detergent solution to remove the olfactory cues of previous animals associated with the chamber.

Novel Object Recognition (NOR):

The NOR test was performed according to the protocol introduced by Ennaceur and Delacour (Ennaceur & Delacour, 1988) with slight modification.

The NOR task procedure consisted of three sessions—habituation, habituation, familiarization and test session. During habituation session, the mouse was placed in an open field (Square box of 40×40×40 cm), facing the wall of the arena, and allowed to explore the entire arena for 10 minutes. Following habituation period of 10 minutes, the mouse was returned to its home cage.

Between every habituation session, the whole arena was cleaned with 10% ethanol to reduce olfactory cues. Twenty-four hours after habituation session, familiarization session of ten minutes was performed. In this session, two identical objects (same texture and shape) were placed 2 cm distant from the walls in the same arena. Test mouse was placed in the open field with its head positioned opposite to the objects and allowed to explore the arena with similar objects for 10 minutes. The video recording of object exploration activity was made to determine the total time spent to explore each object. After 10 minutes of exploration, the mouse was returned back to home cage. Third session-test session was performed after 14 hrs of familiarization session, in which one of the familiar object was replaced by a novel object (of different shape, but same texture). During this session, the test animal was placed in the arena and was allowed to explore the entire arena with familiar and novel object, and its activity was also video recorded. To determine the retention of object memory, the recorded videos of test session were analyzed by independent observer who was unknown to treatment of mice to calculate the time spent in exploring both objects. Data are presented as % time of exploration of familiar or novel object, and discrimination index was calculated as per following equation:

(Tn−Tf)/Tt:   Discrimination Index

Tn=time of exploration with familiar object, Tf=time of exploration with novel object, and Tt=total time of exploration with both type of objects.

Morris Water Maze (MWM) Test:

The Morris water maze (MWM) test was performed according to Morris 1984, with slight modifications. Circular pool of dimensions-100 cm diameter and 45 cm depth, which was filled up to 25 cm from bottom with white colour water. Temperature of water was adjusted to 24-25° C. Pool was divided into four quadrants and a square platform of 10×10 cm in was placed into the tank at a fixed location in the centre of one of the four imaginary quadrants. Training sessions were conducted for 3 consecutive days and on 4$^{th}$ day a probe trial was performed. During training session, mouse was gently placed into the water facing the edge of the pool of one of the quadrant. If the mouse was able to find the platform before the 60 sec cut-off, it was allowed to stay over the platform for 5 more seconds followed by returning to its home cage. Only on the first day of training session, if the mouse did not found the platform, it was placed over the platform manually and allowed to stay there for 20 seconds before returning it to its home cage. Total three trials/day were run for each mouse with minimum interval of 10-15 minutes between two trials, and latency to reach the platform was calculated. On the fourth day, for the probe trial, the platform was removed and the time spent in respective quadrant was calculated.

Our compounds RG-02, RG-04, RG-05 are found to be selective M2 muscarinic receptor agonist with high activity. Moreover in the in-vivo mice model, the compound RG-02 displayed neurostimulatory effect in mice and reversal of scopolamine induced learning and memory deficit. The results obtain clearly suggest the scope of further drug development for compound RG-02 against different pathophysiological conditions involving M2 muscarinic receptor.

Our compounds RG-06 and RG-09 are found to be selective M3 muscarinic receptor antagonist with IC50 activity 9.89 and 9.99 which is tenfold more effective than known drug darifenacin which clearly indicate further scope of drug development against pathophysiological conditions mediated by M3 muscarinic receptors. Moreover compound RG-12 and RG-13 are nonselective muscarinic receptor antagonist against, M1, M3 and M5 muscarinic receptors and hence useful for treatment of associated diseases.

We claim:

1. A substituted methanopyrido [2,1-a]isoindoline selected from the group consisting of (a), (b), (c), (d), (e), (f), a stereoisomer thereof, or a pharmaceutically acceptable salt thereof:

(a) a compound of Formula I

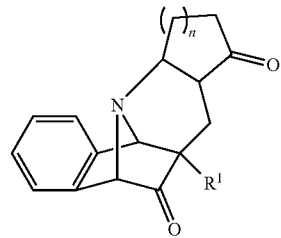

Formula I wherein:

R$^1$ is selected from phenylsulfonyl or p-toluenesulfonyl; and n=1, 2, or 3;

(b) (6S,6aR,11S,12aR)-13-oxo-6-(phenyl sulfonyl)-1,2,3,5,6,6a,11,12a-octahydro-6,11-methanoisoindolo[2,1-a]quinolin-4-yl trifluoromethanesulfonate (RG-12) or its enantiomer:

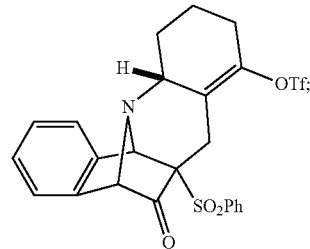

(RG-12)

(c) (6S,6aR,11S,12aR)-13-oxo-6-tosyl-1,2,3,5,6,6a,11,12a-octahydro-6,11-methanoisoindolo[2,1-a]quinolin-4-yl trifluoromethanesulfonate (RG-13) or its enantiomer:

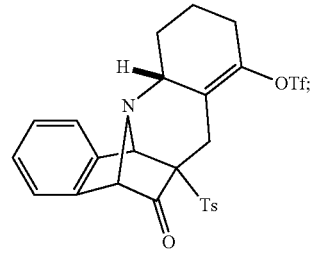

(RG-13)

(d) (4aS,6R,6aR,11S,12aR)-methyl 4-oxo-6-(phenylsulfonyl)-1,2,3,4,4a,5,6,6a,11,12a-decahydroisoindolo[2,1-a]quinoline-11-carboxylate (RG-04) or its enantiomer:

(e) (4aS,6R,6aR,11S,12aR)-ethyl 4-oxo-6-(phenylsulfonyl)-1,2,3,4,4a,5,6,6a,11,12a-decahydroisoindolo[2,1-a]quinoline-11-carboxylate (RG-05) or its enantiomer:

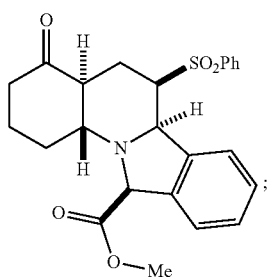

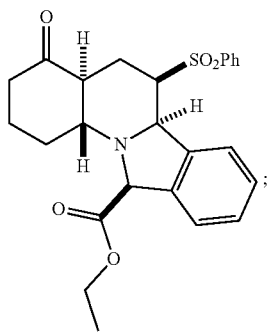

and (f) trifluoroacetate (TFA) salt of (4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione (RG-02) or its enantiomer:

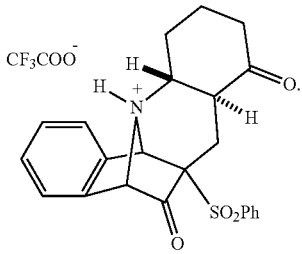

2. The substituted methanopyrido [2,1-a]isoindolone of claim 1, wherein the substituted methanopyrido [2,1-a]isoindolone is a compound of Formula I selected from the group consisting of:

(4aS,6S,6aR,11S,12aR)-6-(phenylsulfonyl)-1,2,3,4a,5,6,6a,12a-octahydro-6,11-methanoisoindolo[2,1-a]quinoline-4,13(11H)-dione (RG-02) or its enantiomer:

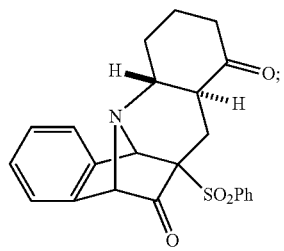

(4aS,6S,6aR,11S,12aR)-6-tosyl-1,2,3,4a,5,6,6a,12a-octahydro-6,11-methanoisoindolo[2,1-a]quinoline-4,13(11H)-dione (RG-06) or its enantiomer:

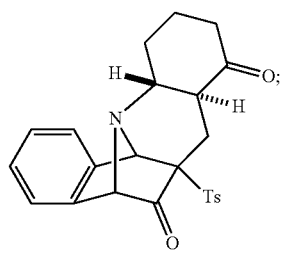

(3aR,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione (RG-09) or its enantiomer:

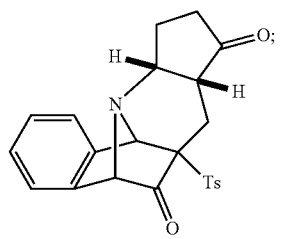

and (3aS,5S,5aR,10S,11aR)-5-tosyl-3a,4,5,5a,10,11a-hexahydro-1H-5,10-methanocyclopenta[5,6]pyrido[2,1-a]isoindole-3,12(2H)-dione (RG-10) or its enantiomer:

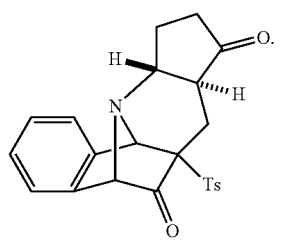

3. The substituted methanopyrido [2,1-a]isoindolone of claim 1, wherein the pharmaceutically acceptable salt is selected from the group consisting of acetate, phenylacetae, trifluoroacetate, ascorbate, benzoate, hydroxybenzoate, methoxybenzoate, methylbenzoate, cinnamate, citrate, formate, fumarate, glycollate, lactate, malate, maleate hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, sulfate, bisulfate, pyrosulfate, sulphite, bisulfate, sulfonate, benzenesulfonate, ethanesulfonate, 2-hydroxyethanesulfonate, methanesulfonate, p-toluenesulfonate, and tartrate.

4. A process for the preparation of the substituted methanopyrido [2,1-a]isoindolone of claim 1, the process comprising:

(i) reacting a compound of formula (a) with a compound of formula (b)

formula (a)

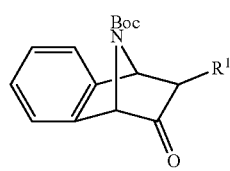

formula (b)

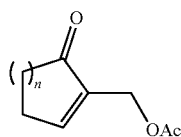

wherein $R^1$ is selected from phenylsulfonyl or p-toluenesulfonyl and n=1, 2, or 3 in presence of a metal catalyst along with a ligand in presence of an inert organic solvents, at a temperature from −20° C. to 80° C., for 1-24 hrs to obtain compound of formula (c)

formula (c)

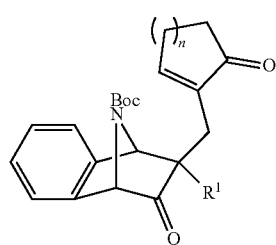

wherein $R^1$ is the same as in formula (a) and n is the same as in formula (b);

(ii) reacting the compound of formula (c) from (i) on deprotection followed by Michael addition at a temperature from −20° C. to 80° C., for 1-24 hrs, to obtain a compound of Formula I Formula I

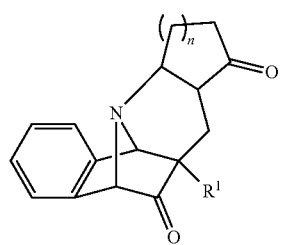

wherein $R^1$ the same as in formula (a) and n is the same as in formula (b); and (iii) optionally performing one of (A), (B), or (C):

(A) converting the compound of Formula I of (ii) with its corresponding enol triflate at a temperature from −20° C. to 80° C., for 6-48 hrs, to obtain a compound of formula (d)

formula (d)

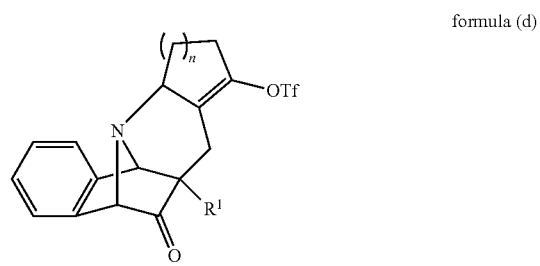

wherein $R^1$ is the same as in formula (a) and n is the same as in formula (b);

(B) reacting the compound of Formula I of (ii) with a nucleophile to undergo C—C bond cleavage at a temperature from 20° C. to 80° C., for 6-48 hrs, to obtain a compound of formula (e)

formula (e)

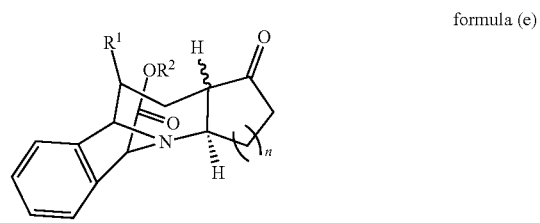

wherein $R^1$ is the same as in formula (a); $R^2$ is alkyl, phenyl, trifluoroethyl, or hydrogen; and n is the same as in formula (b); and (C) reacting the compound of Formula I of (ii) with an acid (H-A) to obtain a corresponding salt of formula (f)

formula (f)

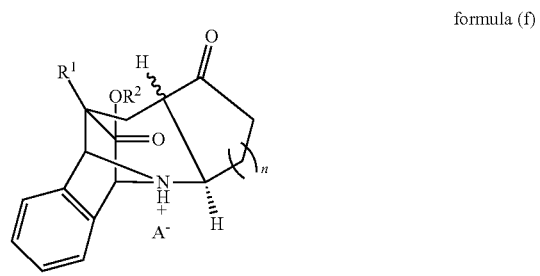

wherein $R^1$ is the same as in formula (a); $R^2$ is alkyl, phenyl, trifluoroethyl, or hydrogen; n is the same as in formula (b); and A is an anion selected from the group consisting of chloride, bromide, iodide, acetate, phenylacetate, trifluoroacetate, ascorbate, benzoate, hydroxybenzoate, methoxybenzoate, methylbenzoate, cinnamate, citrate formate, fumarate, glycollate, lactate, malate, maleate hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate phenylpropionate, salicylate, sebacate, succinate, sulfate, bisulfate, pyrosulfate, sulphite, bisulfate, sulfonate, benzenesulfonate, ethanesulfonate, 2-hydroxyethanesulfonate, methanesulfonate, p-toluenesulfonate, and tartrate.

5. The process of claim 4, wherein the metal catalyst is selected from the group consisting of Pd, Cu, Rh, and Ru.

6. The process of claim 4, wherein the ligand is selected from the group consisting of PBu$_3$, PPh$_3$, P(OPh)$_3$, PPh$_2$(OPh), P(4-F—C$_6$H$_4$)$_3$, 1,2-Bis(diphenylphosphino)ethane (dppe), 1,3-Bis(diphenylphosphino)propane (dppp), and Xantphos.

7. The process of claim 4, wherein the organic solvent is selected from the group consisting of THF, dichloromethane, ethyl acetate, and aromatic hydrocarbon.

8. The process of claim 4, wherein the nucleophile is selected from the group consisting of sodium methoxide and sodium ethoxide.

9. The process of claim 4, wherein the acid is selected from the group consisting of hydrochloric acid, hydrobromic acid, hydroiodic acid, nitric acid, sulfuric acid, phosphoric acid, hypophosphoric acid, trifluoroacetic acid, and acetic acid.

10. A pharmaceutical composition comprising the substituted methanopyrido [2,1-a]isoindolone of claim 1, in combination with drugs that modulate muscarinic receptors and/or one or more pharmaceutically acceptable excipients, the composition comprising from 0.5% to 90% by weight of the substituted methanopyrido [2,1-a]isoindolone, based on the total weight of the composition.

11. The pharmaceutical composition of claim 10, wherein the drugs that modulate muscarinic receptors are selected from group consisting of Xanomeline, Aceclidine, Pilocarpine, Cevimeline, Oxotremorine, Atropine, Scopolamine, Hydroxyzine, Ipratropium, Tropicamide, Pirenzepine, Diphenhydramine, Doxylamine, Dimenhydrinate, Dicyclomine, Flavoxate, Oxyburynin, Titropium, Cyclopentolate, Atropine methonitrate, Trihexylphenidyl/Benzhexol, Tolterodine, Solifenacin, Darifenacin, Benzatropine, Mebeverine, Procyclidine, and Aclidinium bromide.

12. A method for treating a pathophysiological condition associated with muscarinic receptors in a subject in need thereof, the method comprising administering to the subject an effective amount of the substituted methanopyrido [2,1-a]isoindolone according to claim 1 together with one or more pharmaceutical carriers, wherein the pathophysiological condition associated with muscarinic receptors is selected from the group consisting of chronic obstructive pulmonary disease, pulmonary hypertension, dementia, Alzheimer's disease, and schizophrenia.

13. The method of claim 12, wherein the pathophysiological condition associated with muscarinic receptors is selected from the group consisting of chronic obstructive pulmonary disease, pulmonary hypertension, Alzheimer's disease, and schizophrenia.

14. The process of claim 4, wherein n is 2, and wherein (iii) comprises performing (A) to obtain a compound of formula (d) selected from the group consisting of (6S,6aR,11S,12aR)-13-oxo-6-(phenyl sulfonyl)-1,2,3,5,6,6a,11,12a-octahydro-6,11-methanoisoindolo[2,1-a]quinolin-4-yl trifluoromethanesulfonate (RG-12) or its enantiomer:

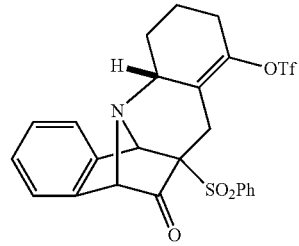

(RG-12)

and (6S,6aR,11S,12aR)-13-oxo-6-tosyl-1,2,3,5,6,6a,11,12a-octahydro-6,11-methanoisoindolo[2,1-a]quinolin-4-yl trifluoromethanesulfonate (RG-13) or its enantiomer:

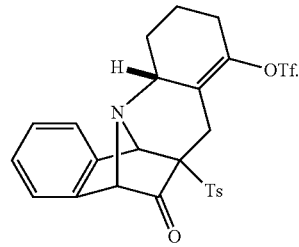

(RG-13)

15. The process of claim 4, wherein n is 2 and R$^1$ is phenylsulfonyl, and wherein (iii) comprises performing (B), wherein the nucleophile is sodium methoxide or sodium ethoxide, to obtain a compound of formula (e) selected from the group consisting of (4aS,6R,6aR,11S,12aR)-methyl-4-oxo-6-(phenylsulfonyl)-1,2,3,4,4a,5,6,6a,11,12a-decahydroisoindolo[2,1-a]quinoline-11-carboxylate (RG-04) or its enantiomer

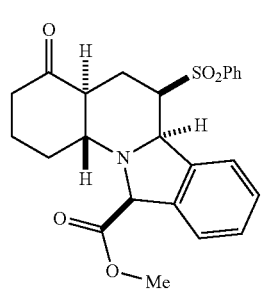

(RG-04)

and (4aS,6R,6aR,11S,12aR)-ethyl 4-oxo-6-(phenylsulfonyl)-1,2,3,4,4a,5,6,6a,11,12a-decahydroisoindolo[2,1-a]quinoline-11-carboxylate (RG-05) or its enantiomer

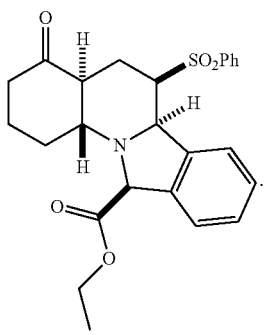
(RG-05)
16. The process of claim 4, wherein n is 2 and $R^1$ is phenylsulfonyl, the process further comprising:
reacting the compound of Formula I with trifluoroacetic acid to obtain a trifluoroacetate (TFA) salt of (4aS,6S, 6aR,11S,12aR)-6-(phenylsulfonyl)-1,2,3,4a,5,6,6a, 12a-octahydro-6,11-methanoisoindolo[2,1-a]quinoline-4,13(11H)-dione (RG-02) or its enantiomer:
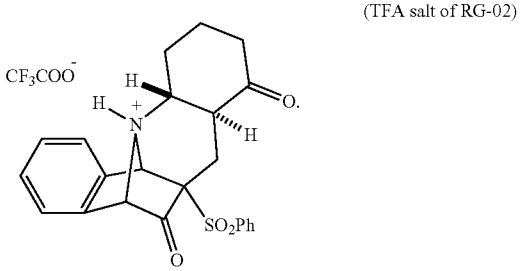
(TFA salt of RG-02)
* * * * *